United States Patent
Schlenoff et al.

(10) Patent No.: US 10,647,953 B2
(45) Date of Patent: May 12, 2020

(54) SURFACE TREATMENT FOR CELL CULTURE

(71) Applicant: The Florida State University Research Foundation, Inc., Tallahassee, FL (US)

(72) Inventors: Joseph B. Schlenoff, Tallahassee, FL (US); Carlos Arias, Tallahassee, FL (US)

(73) Assignee: The Florida State University Research Foundation, Inc., Tallahassee, FL (US)

(*) Notice: Subject to any disclaimer, the term of this patent is extended or adjusted under 35 U.S.C. 154(b) by 1024 days.

(21) Appl. No.: 15/005,115

(22) Filed: Jan. 25, 2016

(65) Prior Publication Data

US 2016/0230136 A1     Aug. 11, 2016

Related U.S. Application Data

(60) Provisional application No. 62/114,745, filed on Feb. 11, 2015.

(51) Int. Cl.
  *C12M 3/00* (2006.01)
  *C12M 1/00* (2006.01)
  *C12M 1/12* (2006.01)

(52) U.S. Cl.
  CPC ............ *C12M 23/20* (2013.01); *C12M 25/02* (2013.01)

(58) Field of Classification Search
  None
  See application file for complete search history.

(56) References Cited

U.S. PATENT DOCUMENTS

| | | | |
|---|---|---|---|
| 3,276,598 A | 10/1966 | Michaels et al. | |
| 3,546,142 A | 12/1970 | Michaels et al. | |
| 3,558,744 A | 1/1971 | Michaels et al. | |
| 3,565,973 A | 2/1971 | Michaels | |
| 4,539,373 A | 9/1985 | Mani et al. | |
| 6,660,367 B1 | 12/2003 | Yang et al. | |
| 6,686,144 B2* | 2/2004 | McLeod | C07K 14/4725 435/4 |
| 6,905,875 B2 | 6/2005 | Yu et al. | |
| 7,101,947 B2 | 9/2006 | Schlenoff et al. | |
| 7,105,229 B2 | 9/2006 | Anderson | |
| 7,223,327 B2 | 5/2007 | Schlenoff et al. | |
| 7,238,536 B1 | 7/2007 | Schlenoff | |
| 7,387,824 B2 | 6/2008 | Tamagawa et al. | |
| 2004/0265603 A1 | 12/2004 | Schlenoff | |
| 2005/0176620 A1 | 8/2005 | Prestwich et al. | |
| 2005/0282925 A1 | 12/2005 | Schlenoff et al. | |
| 2005/0287111 A1* | 12/2005 | Schlenoff | A61K 31/785 424/78.3 |
| 2006/0051532 A1 | 3/2006 | Tamagawa et al. | |
| 2006/0065529 A1 | 3/2006 | Schlenoff et al. | |
| 2006/0073333 A1 | 4/2006 | Anderson | |
| 2007/0259452 A1 | 11/2007 | Schlenoff | |
| 2007/0265174 A1 | 11/2007 | Schlenoff | |
| 2012/0027837 A1* | 2/2012 | DeMuth | A61K 9/0021 424/443 |

OTHER PUBLICATIONS

Allen, Norman S., "Polymer Photochemistry", Photochemistry, 2007, vol. 36, pp. 232-297.
Biggerstaff et al., "Damping Performance of Cocured Graphite/Epoxy Composite Laminates with Embedded Damping Materials", Journal of Composite Materials, 1999, vol. 33, No. 15, pp. 1457-1469.
Dai et al., "Controlling the Permeability of Multilayered Polyelectrolyte Films through Derivatization, Cross-Linking, and Hydrolysis", Langmuir, 2001, vol. 17, No. 3, pp. 931-937.
Dubas et al., "Swelling and Smoothing of Polyelectrolyte Multilayers by Salt", Langmuir, 2001, vol. 17, pp. 7725-7727.
Graul et al., "Capillaries Modified by Polyelectrolyte Multilayers for Electrophoretic Separations", Analytical Chemistry, 1999, vol. 71, No. 18, pp. 4007-4013.
Holmlin et al., "Zwitterionic SAMs that Resist Nonspecific Adsorption of Protein from Aqueous Buffer", Langmuir, 2001, vol. 17, No. 9, pp. 2841-2850.
Iatridis et al., "The Viscoelastic Behavior of the Non-Degenerate Human Lumbar Nucleus Pulposus in Shear", J. Biomechanics, 1997, vol. 30, No. 10, pp. 1005-1013.
Iatridis et al., "Shear Mechanical Properties of Human Lumbar Annulus Fibrosus", Journal of Orthopaedic Research, 1999, vol. 17, No. 5, pp. 732-737.
Jaber et al., "Mechanical Properties of Reversibly Cross-Linked Ultrathin Polyelectrolyte Complexes", Journal of American Chemical Society, 2006, vol. 128, pp. 2940-2947.
Kozlovskaya et al., "Hydrogen-Bonded Polymer Capsules Formed by Layer-by-Layer Self-Assembly", Macromolecules, 2003, vol. 36, pp. 8590-8592.
Lim et al., "Microencapsulated Islets as Bioartificial Endocrine Pancreas", Science, New Series, 1980, vol. 210, No. 4472, pp. 908-910.
Losche et al., "Detailed Structure of Molecularly Thin Polyelectrolyte Multilayer Films on Solid Substrates as Revealed by Neutron Reflectometry", Macromolecules, 1998, vol. 31, No. 25, pp. 8893-8906.
Michaels, Alan S., "Polyelectrolyte Complexes", Industrial & Engineering Chemistry, 1965, vol. 57, No. 10, pp. 32-40.
Rosidian et al., "Ionic Self-Assembly of Ultrahard ZrO2/Polymer Nanocomposite Thin Films", Advanced Materials, 1998, vol. 10, No. 14, pp. 1087-1091.

(Continued)

*Primary Examiner* — Julie Wu
*Assistant Examiner* — Douglas F White
(74) *Attorney, Agent, or Firm* — Armstrong Teasdale LLP

(57) ABSTRACT

An article suitable for inducing quasispherical cell clustering is provided. The article comprising: a layer suitable for culturing quasispherical cell clusters, the layer comprising a bulk region comprising an interpenetrating network of at least one predominantly positively charged polyelectrolyte and at least one predominantly negatively charged positive polyelectrolyte, a back surface region, and a front surface region, wherein the front surface region comprises a net negative fixed surface charge density of between about 0.4 micromole per $m^2$ and about 1.5 micromole per $m^2$.

22 Claims, 9 Drawing Sheets

(56) References Cited

OTHER PUBLICATIONS

Smets, G., "Photocross-Linkable Polymers", Journal of Macromolecular Science Chemistry, 1984, A21(13 & 14), pp. 1695-1703.
Strehmel, Veronika, "Epoxies: Structures, Photoinduced Cross-Linking, Network Properties, and Applications", Handbook of Photochemistry and Photobiology, 2003, Chapter 1, pp. 1-110.
Sui et al., "Phase Separations in pH-Responsive Polyelectrolyte Multilayers: Charge Extrusion versus Charge Expulsion", Langmuir, 2004, vol. 20, No. 14, pp. 6026-6031.
Timpe, Hans-Joachim, "Polymer Photochemistry and Photo-Cross-Linking", Desk Reference of Functional Polymers: Syntheses and Applications, 1997, pp. 273-291.
Poly(Ethylene Glycol) Chemistry: Biotechnical and Biomedical Applications (Table of Contents only), Edited by Milton J. Harris, 1992, Plenum Press, New York, New York, 13 pages.
R. Reese Handbook of Antibiotics (Table of Contents and Preface only), Third Edition, 2000, 3 pages, Lippincott Williams and Wilkins, Philadelphia, Pennsylvania.
International Search Report, PCT/US2007/77146, dated Mar. 7, 2008, 2 pages.
Written Opinion of the International Searching Authority, PCT/US2007/77146, dated Mar. 7, 2008, 8 pages.
Sarobe, J. et al., "Functionalized Monodisperse Particles with Chloromethyl Groups for the Covalent Coupling of Proteins," Macromolecules, 1998, vol. 31, pp. 4282-4287.

* cited by examiner

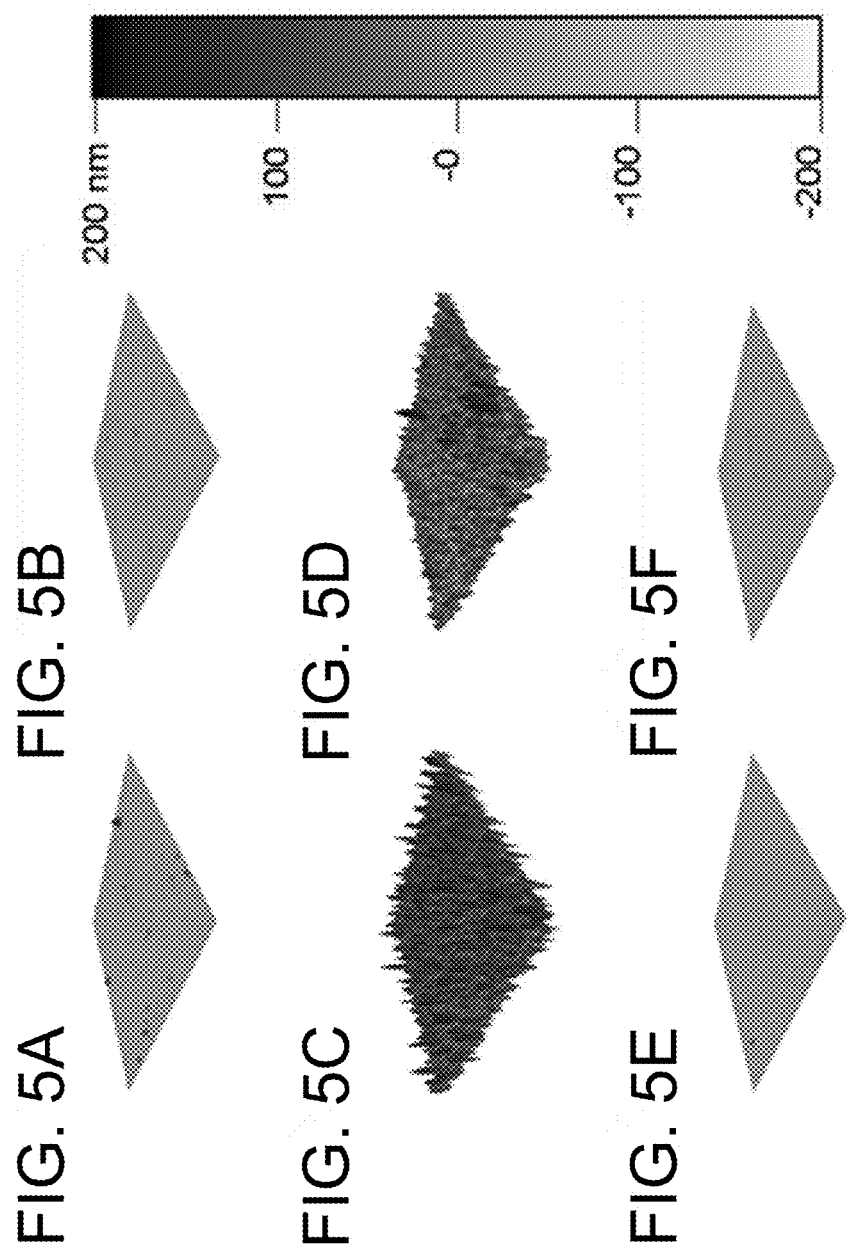

SURFACE TREATMENT FOR CELL CULTURE

CROSS REFERENCE TO RELATED APPLICATION(S)

This application claims the benefit of U.S. Provisional Application Ser. No. 62/114,745 filed Feb. 11, 2015 and titled "Surface Treatment for Cell Culture." U.S. Provisional Application Ser. No. 62/114,745 is incorporated by reference as if set forth in its entirety.

STATEMENT REGARDING FEDERALLY SPONSORED RESEARCH OR DEVELOPMENT

This invention was made with Government support under Grant No. DMR 1207188 awarded by the National Science Foundation. The Government has certain rights in the invention.

FIELD OF THE INVENTION

The present invention relates to a polyelectrolyte surface coating to induce clustering of cells and methods of forming said coating.

BACKGROUND OF THE INVENTION

In order for cells to adhere and grow on a substrate, the interface between the substrate and the cell growth medium must possess an appropriate combination of physical and chemical properties. Control over the surface of substrate provides for control over cell adhesion. Advantageous properties imparted by a surface range from the complete rejection of any cell adhesion or growth, to cell adhesion without growth, to cell adhesion, growth, and differentiation. The property desired depends on the end-use of the substrate. For example, articles implanted in vivo, such as stents, catheters, and artificial organs, preferably do not induce biochemical processes that lead to scarring and/or rejection of said article. These implants may be advantageously coated with thin films that render them biocompatible. Alternatively, some applications, especially those in tissue engineering, require substrates that encourage the growth, differentiation, and proliferation of cells.

Recent studies have shown that some cells need to aggregate and interact with neighboring cells in a 3-D environment in order to activate or enhance metabolic activity, (see Kurosawa, H., Methods for inducing embryoid body formation: in vitro differentiation system of embryonic stem cells. Journal of Bioscience and Bioengineering 2007, 103, (5), 389-398) and extracellular matrix production. Cell aggregates or cell spheroids of human mesenchymal (hMSCs) and pluripotent stem cells (PSCs) have demonstrated promise in cellular therapy and tissue engineering. These aggregates are usually formed by suspension culture techniques, where the cells are cultured under orbital shaking or magnetic stirring with special media to prevent differentiation, or using coated microcarrier technology, where cells proliferate onto small particles suspended in media (e.g., see U.S. Pat. No. 8,716,018 issued to Oh et al.).

Control over surface properties is maintained by an appropriately-designed coating. Ultrathin films of polyelectrolyte complex, or polyelectrolyte multilayers (PEMUs) are prepared by alternating exposure of the substrate to polyelectrolytes or charged particles. See Decher and Schlenoff, Eds., *Multilayer Thin Films—Sequential Assembly of Nanocomposite Materials*, Wiley-VCH, Weinheim (2003); Decher, *Science,* 277, 1232 (1997). Decher and Hong (U.S. Pat. No. 5,208,111) disclose a method for a buildup of multilayers by alternating dipping, i.e., cycling a substrate between two reservoirs containing aqueous solutions of polyelectrolytes of opposite charge, with an optional rinse step in polymer-free solution following each immersion.

The large library of materials available for this layer-by-layer assembly enables precise tailoring of surface properties for cell culture. There have been many reports on cells cultured on substrates modified with multilayers. While most multilayers allow some degree of cell attachment, spreading, and proliferation, others effectively prevent cells adhesion. Cell adhesion is a complex, dynamic process, even in the absence of specific interactions. The multitude of physical factors playing a role in cell attachment onto multilayers include surface roughness, wettability, swelling, internal ionic crosslinking, thickness, surface charge, and mechanical properties.

Previous observations show no correlation of cell attachment with one unique parameter. However, depending on the cell type some parameters may influence surface attachment more than others. A good deal of contradiction exists. For example, when it comes to the importance of surface charge, prior research concludes that cells can, or cannot, adhere to both positively and negatively charged surfaces, even though the toxicity of polycations is well documented. Such studies usually focus on the sign of the charge on the surface, but rarely determine the actual charge density.

For cell culture there is a need for a simple, rugged surface coating that induces cells to form clusters.

SUMMARY OF THE INVENTION

In some specific embodiments of the invention, fibroblasts cultured on polyelectrolyte multilayers, PEMUs, made from poly(diallyldimethylammonium), PDADMA, and poly(styrene sulfonate), PSS, showed a variety of attachment modes, depending on the charge of the last layer and deposition conditions. PEMUs terminated with PDADMA (cationic) were cytotoxic when built in 1.0 M NaCl but cytophilic when built in 0.15 M NaCl. Cells adhered poorly to all PSS-capped (anionic) films. PEMUs built in 0.15 M NaCl but terminated with a layer of PSS in 1.0 M NaCl induced most cells to form spherical clusters after about 48 hours of culture. These clusters still interrogated the surface and when they were replated on control tissue culture plastic, cells emerged with close to 100% viability. Differences between the various surfaces were probed in an effort to identify the mechanism responsible for this unusual behavior, which did not follow accepted correlations between substrate stiffness and cell adhesion. No significant differences in roughness or wetting were observed between cluster-inducing PSS-capped multilayers and those that did not produce clusters. When the surface charge was assayed with radiolabeled ions a strong increase of negative fixed surface charge was revealed. Viewing the multilayer as a zwitterionic solid and comparing its surface charge density to that of a cell membrane yields similarities that suggest a mechanism for preventing protein adhesion to the surface, a necessary step in the integrin-mediated mechanotransduction properties of a cell.

Accordingly, among the various aspects of the present invention may be noted an article comprising a layer suitable for culturing quasispherical cell clusters, the layer comprising a bulk region comprising an interpenetrating network of at least one predominantly positively charged polyelectrolyte and at least one predominantly negatively charged polyelectrolyte, a back surface region, and a front surface region, wherein the front surface region comprises a net negative fixed surface charge density of between about 0.5 micromole per m² and about 1.5 micromole per m².

The present invention is further directed to a method of depositing a coating on a substrate, the method comprising: depositing polyelectrolyte complex on an exposed surface of the substrate, the polyelectrolyte complex comprising interpenetrating network of at least one predominantly positively charged polyelectrolyte and at least one predominantly negatively charged polyelectrolyte, the interpenetrating network comprising a back surface region in contact with the exposed surface of the substrate, a bulk region, and a front surface region; and contacting the front surface region of the interpenetrating network with a conditioning solution comprising a predominantly negatively charged polyelectrolyte and a conditioning salt to thereby deposit the predominantly negatively charged polyelectrolyte on the front surface region of the interpenetrating network, wherein said deposition of the predominantly negatively charged polyelectrolyte fixes the negative charge density of the front surface region of the interpenetrating network to a net negative fixed surface charge density of between about 0.5 micromole per m² and about 1.5 micromole per m².

The present invention is still further directed to a method for culturing cells, the method comprising: plating cells upon a front surface region of a layer suitable for culturing quasispherical cell clusters, the layer comprising a bulk region comprising an interpenetrating network of at least one predominantly positively charged polyelectrolyte and at least one predominantly negatively charged positive polyelectrolyte, a back surface region, and the front surface region, wherein the front surface region comprises a net negative fixed surface charge density of between about 0.5 micromole per m² and about 1.5 micromole per m²; wherein said plating the cells upon the front surface region of the layer induces the cells to cluster into quasispherical cell clusters.

Other objects and features will be in part apparent and in part pointed out hereinafter.

BRIEF DESCRIPTION OF THE DRAWINGS

(FIG. 1A) [PDADMA/PSS, 1.0]$_{10}$ (PSS ending layer), (FIG. 1B) [PDADMA/PSS, 0.15]$_{10}$ (PSS ending layer), (FIG. 1C) [PDADMA/PSS, 1.0]$_{10}$[PDADMA, 1.0] (PDADMA ending layer), (FIG. 1D) [PDADMA/PSS, 0.15]$_{10}$[PDADMA, 0.15] (PDADMA ending layer), (FIG. 1E) Tissue culture plastic, TCP, (polystyrene) control surface. Scale bar 100 µm.

(FIG. 3A) [PDADMA/PSS, 1.0]$_9$[PDADMA, 1.0][PSS, 0.15] (PSS ending layer), (FIG. 3B) [PDADMA/PSS, 0.15]$_9$ [PDADMA, 0.15][PSS, 1.0] (PSS ending layer), (FIG. 3C) [PDADMA/PSS, 1.0]$_{10}$[PDADMA, 0.15] (PDADMA ending layer), (FIG. 3D) [PDADMA/PSS, 0.15]$_{10}$[PDADMA, 1.0] (PDADMA ending layer). Scale bar 100 µm.

(FIG. 4A) Frame from live cell imaging of individual cells scanning the surface of a [PDADMA/PSS, 0.15]$_9$ [PDADMA, 0.15][PSS, 1.0] film, the cells extend their lamellipodia (highlighted in boxes) in different directions but do not attach to the substrate. Scale bar 10 µm (FIG. 4B) fibroblasts leaving a quasi-spherical cluster after being reseeded onto an uncoated polystyrene control surface. Scale bar 100 µm.

FIGS. 5A through 5F are 20×20 µm AFM images acquired in dry and wet conditions of hybrid and native PDADMA/PSS polyelectrolyte multilayers PSS ending layer. (FIG. 5A) dry Native 0.15M, (FIG. 5B) wet Native 0.15M, (FIG. 5C) dry Native 1.0M, (FIG. 5D) wet Native 1.0M, (FIG. 5E) dry Hybrid, (FIG. 5F) wet Hybrid.

DESCRIPTION OF THE EMBODIMENT(S) OF THE INVENTION

Figure 1C:
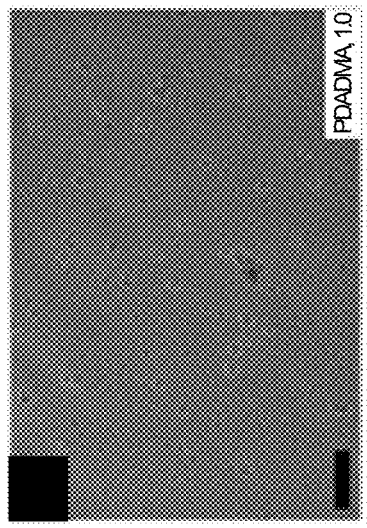
FIGS. 1A through 1E are phase contrast micrographs acquired on day 3 of live 3T3 fibroblasts seeded at 10,000 cells cm$^{-2}$ onto PDADMA/PSS polyelectrolyte multilayers prepared at different salt concentrations. Text in lower right shows the top layer and [NaCl] used for buildup.

One aspect of the invention is a layer or coating comprising a polymer, in particular, a polymer known as a "polyelectrolyte" that comprises multiple electrolytic repeat units that dissociate in solutions, making the polymer charged. The layer or coating of the present invention comprises a polyelectrolyte complex, that is, an intermolecular blend of a predominantly positively-charged polyelectrolyte and a predominantly negatively-charged polyelectrolyte. The polyelectrolyte complex is preferably in the form of an ultrathin film, typically achieved by multilayering (as described for example in *Science*, 277 p 1232-1237 (1997)).

In general, a polyelectrolyte complex is formed by combining a predominantly negatively charged polyelectrolyte and a predominantly positively charged polyelectrolyte. In a preferred embodiment, the polyelectrolyte complex thin film, PECTF, uses alternating exposure of a substrate to solutions each containing one of the polyelectrolytes; in this embodiment, at least one solution comprises at least one predominantly positively-charged polyelectrolyte, and at least one solution comprises at least one predominantly negatively-charged polyelectrolyte. The formation of a polyelectrolyte complex ion pair, Pol⁺Pol⁻, by layering individual solutions of the polyelectrolytes in their respective salt forms, $Pol^+A^-$ and $Pol^-M^+$, may be represented by the following equation:

$$Pol^+A^- + Pol^-M^+ \rightarrow Pol^+Pol^- + MA$$

where $M^+$ is a salt cation, such as sodium, and $A^-$ is a salt anion such as chloride. $Pol^-$ and $Pol^+$ represent repeat units on predominantly negatively charged and predominantly positively charged polyelectrolytes, respectively. According to the equation, the process of complexation releases salt ions into external solution, which are then part of the salt solution concentration.

Individual polyelectrolyte solutions that are mixed may themselves comprise mixtures of polyelectrolytes of different chemical composition and/or molecular weight. For example, a solution may comprise two positive polyelectrolytes with two distinct chemical compositions. When the mixture of positive polyelectrolytes is layered with the negative polyelectrolyte solutions the resulting complex will incorporate a blend of the two positive polyelectrolytes. Such a strategy is described for example in U.S. Pat. No. 7,722,752.

Polyelectrolytes for Complexes

The charged polymers (i.e., polyelectrolytes) used to form the polyelectrolyte complex thin film, PECTF, are water soluble and/or organic soluble and comprise one or more monomer repeat units that are positively or negatively charged. The polyelectrolytes used in the present invention may be copolymers that have a combination of charged and/or neutral monomers (e.g., positive and neutral; negative and neutral; positive and negative; or positive, negative, and neutral). Regardless of the exact combination of charged and neutral monomers, a polyelectrolyte of the present invention is predominantly positively charged or predominantly negatively charged and hereinafter is referred to as a "positively charged polyelectrolyte" or a "negatively charged polyelectrolyte," respectively.

Alternatively, the polyelectrolytes can be described in terms of the average charge per repeat unit in a polymer chain. For example, a copolymer composed of 100 neutral and 300 positively charged repeat units has an average charge of 0.75 (3 out of 4 units, on average, are positively charged). As another example, a polymer that has 100 neutral, 100 negatively charged, and 300 positively charged repeat units would have an average charge of 0.4 (100 negatively charged units cancel 100 positively charged units leaving 200 positively charged units out of a total of 500 units). Thus, a positively-charged polyelectrolyte has an average charge per repeat unit between 0 and 1 and a negatively-charged polyelectrolyte has an average charge per repeat unit between 0 and −1. An example of a positively-charged copolymer is PDADMA-co-PAC (i.e., poly (diallyldimethylammonium chloride) and polyacrylamide copolymer) in which the PDADMA units have a charge of 1 and the PAC units are neutral so the average charge per repeat unit is less than 1.

Some polyelectrolytes comprise equal numbers of positive repeat units and negative repeat units distributed throughout the polymer in a random, alternating, or block sequence. These polyelectrolytes are termed "amphiphilic" polyelectrolytes. For examples, a polyelectrolyte molecule may comprise 100 randomly distributed styrene sulfonate repeat units (negative) and 100 diallyldimethylammonium chloride repeat units (positive), said molecule having a net charge of zero. If charges on one amphiphilic polymer associate with charges on another the material is considered a polyelectrolyte complex.

Some polyelectrolytes comprise a repeat unit that has both a negative and positive charge. Such repeat units are termed "zwitterionic" and the polyelectrolyte is termed a "zwitterionic polyelectrolyte." Though zwitterionic repeat units contribute equal number of positive and negative repeat units, the zwitterionic group is still solvated and relatively hydrophilic.

Since the role of zwitterions groups is to reduce fouling of a polyelectrolyte complex, the location of the zwitterion groups within a PECTF is preferably at the outer surface.

The charges on a polyelectrolyte may be derived directly from the monomer units, or they may be introduced by chemical reactions on a precursor polymer. For example, PDADMA is made by polymerizing diallyldimethylammonium chloride, a positively charged water soluble vinyl monomer. PDADMA-co-PAC is made by the polymerization of a mixture of diallyldimethylammonium chloride and acrylamide (a neutral monomer which remains neutral in the polymer). Poly(styrenesulfonic acid) is often made by the sulfonation of neutral polystyrene. Poly(styrenesulfonic acid) can also be made by polymerizing the negatively charged styrene sulfonate monomer. The chemical modification of precursor polymers to produce charged polymers may be incomplete and typically result in an average charge per repeat unit that is less than 1. For example, if only about 80% of the styrene repeat units of polystyrene are sulfonated, the resulting poly(styrenesulfonic acid) has an average charge per repeat unit of about −0.8.

Examples of a negatively-charged synthetic polyelectrolyte include polyelectrolytes comprising a sulfonate group ($-SO_3^-$), such as poly(styrenesulfonic acid) (PSS), poly(2-acrylamido-2-methyl-1-propane sulfonic acid) (PAMPS), sulfonated poly (ether ether ketone) (SPEEK), poly(ethylenesulfonic acid), poly(methacryloxyethylsulfonic acid), their salts, and copolymers thereof; polycarboxylates such as poly(acrylic acid) (PAA) and poly(methacrylic acid), polyphosphates, and polyphosphonates.

Examples of a positively-charged synthetic polyelectrolyte include polyelectrolytes comprising a quaternary ammonium group, such as poly(diallyldimethylammonium chloride) (PDADMA), poly(vinylbenzyltrimethylammonium) (PVBTA), ionenes, poly(acryloxyethyltrimethyl ammonium chloride), poly(methacryloxy(2-hydroxy)propyltrimethyl ammonium chloride), and copolymers thereof; polyelectrolytes comprising a pyridinium group such as poly(N-methylvinylpyridinium) (PMVP), including poly(N-methyl-2-vinylpyridinium) (PM2VP), other poly(N-alkylvinylpyridines), and copolymers thereof; protonated polyamines such as poly(allylaminehydrochloride) (PAH), polyvinylamine, polyethyleneimine (PEI); polysulfoniums, and polyphosphoniums.

Exemplary polyelectrolyte repeat units, both positively charged and negatively charged, are shown in Table I.

TABLE I

| Polyelectrolyte Repeat Units | |
|---|---|
| Name | Structure |
| diallyldimethylammonium (PDADMA) | 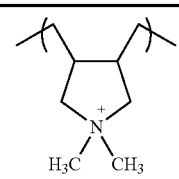 |

TABLE I-continued

Polyelectrolyte Repeat Units

| Name | Structure |
| --- | --- |
| styrenesulfonic acid (PSS) | (structure with phenyl-$SO_3^-$) |
| N-methyl-2-vinyl pyridinium (PM2VP) | (structure with 2-pyridinium-$CH_3$) |
| N-methyl-4-vinylpyridinium (PM4VP) | (structure with 4-pyridinium-$CH_3$) |
| N-octyl-4-vinylpyridinium (PNO4VP) | (structure with 4-pyridinium-octyl) |
| N-methyl-2-vinyl pyridinium-co-ethyleneoxide (PM2VP-co-PEO) | (copolymer structure; X and Y denote proportions of repeat units) |
| acrylic acid (PAA) | (structure with $COO^-$) |
| Allylamine (PAH) | (structure with $NH_3^+$) |
| ethyleneimine (PEI) | (structure with NH) |

Further examples of polyelectrolytes include charged biomacromolecules, which are naturally occurring polyelectrolytes, or synthetically modified charged derivatives of naturally occurring biomacromolecules, such as modified celluloses, chitosan, or guar gum. A positively-charged biomacromolecule usually comprises a protonated sub-unit (e.g., protonated amines). Some negatively charged biomacromolecules comprise a deprotonated sub-unit (e.g., deprotonated carboxylates or phosphates). Examples of biomacromolecules which may be charged for use in accordance with the present invention include proteins, polypeptides, enzymes, DNA, RNA, glycosaminoglycans, alginic acid, chitosan, chitosan sulfate, cellulose sulfate, polysaccharides, dextran sulfate, carrageenin, hyaluronic acid, sulfonated lignin, and carboxymethylcellulose.

Some advantages of these naturally occurring polyelectrolytes are that they may be inexpensive, widely available, and nontoxic. Other properties of these naturally occurring polyelectrolytes are that their complexes can be soft and hydrated and they may be degraded or consumed by natural organisms.

Natural, or biological, polyelectrolytes typically exhibit greater complexity in their structure than synthetic polyelectrolytes. For example, proteins may comprise any combination of about 2 dozen amino acid building blocks, some charged, which are natural repeat units. Polymeric nucleic acids such as DNA and RNA may also comprise many different monomer repeat units ("nucleobases"). The sign and magnitude of the charge on proteins depends on the solution pH, as the charge on proteins is carried by weak acids, such as carboxylates (—COOH), or weak bases, such as primary, secondary, and tertiary amines. Thus, at high pH (basic conditions) amines are deprotonated and uncharged, and carboxylate groups are deprotonated and charged. At low pH (acidic conditions) amines are protonated and charged, and carboxylate groups are protonated and uncharged. For proteins, there is a pH at which there are equal numbers of positive and negative charges on the biomolecule, and it is thus electrically neutral. This is termed the isoelectric point, or pI. At pH above the isoelectric point, the protein has a net negative charge and at pH below pI, proteins bear a net positive charge. Proteins that tend to have a preponderance of positive charge at physiological pH, characterized by a high pI, are often termed "basic" proteins, and proteins with a low pI are called "acidic" proteins.

The molecular weight (number average) of synthetic polyelectrolyte molecules is typically about 1,000 to about 5,000,000 grams/mole, preferably about 10,000 to about 1,000,000 grams/mole. The molecular weight of naturally occurring polyelectrolyte molecules (i.e., biomacromolecules), however, can reach as high as 10,000,000 grams/mole. The polyelectrolyte solutions that are layered to prepare PECTF typically comprise about 0.001% to about 50% by weight of a polyelectrolyte, and preferably about 0.01% to about 10% by weight.

Many of the foregoing polymers/polyelectrolytes, such as PEI, exhibit some degree of branching. Branching may occur at random or at regular locations along the backbone of the polymer. Branching may also occur from a central point and in such a case the polymer is referred to as a "star" polymer, if generally linear strands of polymer emanate from the central point. If, however, branching continues to propagate away from the central point, the polymer is referred to as a "dendritic" polymer. Branched polyelectrolytes, including star polymers, comb polymers, graft polymers, and dendritic polymers, are also suitable for purposes of this invention. Block polyelectrolytes, wherein a macromolecule comprises at least one block of charged repeat units, are also suitable. The number of blocks may be 2 to 5. Preferably, the number of blocks is 2 or 3. If the number of blocks is 3 the block arrangement is preferably ABA.

Many of the foregoing polyelectrolytes have very low toxicity. For example, poly(diallyldimethylammonium chloride), poly(2-acrylamido-2-methyl-1-propane sulfonic acid) and their copolymers are used in the personal care industry, e.g., in shampoos. Also, because the preferred polyelectrolytes used in the method of the present invention are synthetic or synthetically modified natural polymers, their properties (e.g., charge density, viscosity, water solubility, and response to pH) may be tailored by adjusting their composition.

By definition, a polyelectrolyte solution comprises a solvent. An appropriate solvent is one in which the selected polyelectrolyte is soluble. Thus, the appropriate solvent is dependent upon whether the polyelectrolyte is considered to be hydrophobic or hydrophilic. A hydrophobic polymer displays a less favorable interaction energy with water than a hydrophilic polymer. While a hydrophilic polymer is water soluble, a hydrophobic polymer may only be sparingly soluble in water, or, more likely, insoluble in water. Likewise, a hydrophobic polymer is more likely to be soluble in organic solvents than a hydrophilic polymer. In general, the higher the carbon to charge ratio of the polymer, the more hydrophobic it tends to be. For example, polyvinyl pyridine alkylated with a methyl group (PNMVP) is considered to be hydrophilic, whereas polyvinyl pyridine alkylated with an octyl group (PNOVP) is considered to be hydrophobic. Thus, water is preferably used as the solvent for hydrophilic polyelectrolytes and organic solvents such as ethanol, methanol, dimethylformamide, acetonitrile, carbon tetrachloride, and methylene chloride are preferably used for hydrophobic polyelectrolytes. Fluorinated solvents are preferred for fluorinated polyelectrolytes. Even if polyelectrolyte complexes are prepared by mixing organic-soluble and water-soluble polymers, the starting polyelectrolyte complex is preferably rinsed to remove organic solvents before it is processed according to the method described herein. Some organic solvents are hard to remove even with extensive rinsing. Therefore, the preferred solvent for polyelectrolyte complexation is water.

Examples of polyelectrolytes that are soluble in water include poly(styrenesulfonic acid), poly(2-acrylamido-2-methyl-1-propane sulfonic acid), sulfonated lignin, poly(ethylenesulfonic acid), poly(methacryloxyethylsulfonic acid), poly(acrylic acids), poly(methacrylic acids), their salts, and copolymers thereof; as well as poly(diallydimethylammonium chloride), poly(vinylbenzyltrimethylammonium), ionenes, poly(acryloxyethyltrimethyl ammonium chloride), poly(methacryloxy(2-hydroxy)propyltrimethyl ammonium chloride), and copolymers thereof; and polyelectrolytes comprising a pyridinium group, such as, poly(N-methylvinylpyridium), and protonated polyamines, such as, poly(allylamine hydrochloride), polyvinylamine and poly(ethyleneimine).

Examples of polyelectrolytes that are soluble in non-aqueous solvents, such as ethanol, methanol, dimethylformamide, acetonitrile, carbon tetrachloride, and methylene chloride include poly(N-alkylvinylpyridines), and copolymers thereof in which the alkyl group is longer than about 4 carbon atoms. Other examples of polyelectrolytes soluble in organic solvents include poly(styrenesulfonates), poly(diallyldimethylammonium), poly(N-alkylvinylpyridinium), poly(alkylimidazoles), poly(vinylbenzylalkylammoniums) and poly(ethyleneimine) where the small inorganic counterion, such as, sodium, potassium, chloride or bromide, has been replaced by a hydrophobic counterion such as tetrabutyl ammonium, tetraethyl ammonium, tetraalkylammonium, alkylammonium, alkylphosphonium, alkylsulfonium, alkylimidazolium, alkylpiperidinium, alkylpyridinium, alkylpyrazolium, alkylpyrrolidinium, iodine, alkylsulfate, arylsulfonates, hexafluorophosphate, tetrafluoroborate, trifluoromethane sulfonate, hexfluorphosphate or bis(trifluoromethane)sulfonimide.

Some polyelectrolytes comprise rigid rod backbones, such as aromatic backbones, or partially aromatic backbones, including sulfonated polyparaphenylene, sulfonated polyetherether ketones (SPEEK), sulfonated polysulfones, sulfonated polyarylenes, sulfonated polyarylene sulfones, and polyarylenes comprising alkylammonium groups.

The charged polyelectrolyte may be a synthetic copolymer comprising pH sensitive repeat units, pH insensitive repeat units, or a combination of pH sensitive repeat units and pH insensitive repeat units. pH insensitive repeat units maintain the same charge over the working pH range of use. The rationale behind such a mixture of pH sensitive groups and pH insensitive groups on the same molecule is that the pH insensitive groups interact with other, oppositely-charged pH insensitive groups on other polymers, holding the multilayer together despite the state of ionization of the pH sensitive groups.

For example, poly(acrylic acids) and derivatives begin to take on a negative charge within the range of about pH 4 to about 6 and are negatively charged at higher pH levels. Below this transition pH range, however, poly(acrylic acids) are protonated (i.e., uncharged). Similarly, polyamines and derivative thereof take on a positive charge if the pH of the solution is below their $pK_a$. As such, and in accordance with the present invention, the pH of a polyelectrolyte solutions and rinsing solutions may be adjusted by the addition of an acid and/or base in order to attain, maintain, and/or adjust the electrical charge of a polyelectrolyte at the surface of, or within, a PECTF.

The state of ionization, or average charge per repeat unit, for polyelectrolytes bearing pH sensitive groups depends on the pH of the solution. For example, a polyelectrolyte comprising 100 pH insensitive positively charged units, such as DADMA, and 30 pH sensitive negatively charged units, such as acrylic acid, AA, will have a net charge of +100 at low pH (where the AA units are neutral) and an average of +100/130 charge per repeat unit; and a net charge of +70 at high pH (where 30 ionized AA units cancel out 30 of the positive charges) and an average of +70/130 charge per repeat unit. The different monomer units may be arranged randomly along the polymer chain ("random" copolymer) or they may exist as blocks ("block" copolymer). The average charge per repeat unit is also known as the "charge density."

pH sensitive polyelectrolyte complexes comprise pH sensitive polymeric repeat units, selected for example, from moieties containing carboxylates, pyridines, imidazoles, piperidines, phosphonates, primary, secondary and tertiary amines, and combinations thereof. Therefore, preferred polyelectrolytes used in accordance with this invention include copolymers comprising carboxylic acids, such as poly(acrylic acids), poly(methacrylic acids), poly(carboxylic acids), and copolymers thereof. Additional preferred polyelectrolytes comprise protonatable nitrogens, such as poly(pyridines), poly(imidazoles), poly(piperidines), and poly(amines) bearing primary, secondary or tertiary amine groups, such as poly(vinylamines) and poly(allylamine).

To avoid disruption and possible decomposition of the polyelectrolyte complex, polyelectrolytes comprising pH sensitive repeat units additionally comprise pH insensitive charged functionality on the same molecule. In one embodiment, the pH insensitive repeat unit is a positively charged repeat unit selected from the group consisting of repeat units containing a quaternary nitrogen atom, a sulfonium ($S^+$) atom, or a phosphonium atom. Thus, for example, the quaternary nitrogen may be part of a quaternary ammonium moiety (—$N^+R_aR_bR_c$ wherein $R_a$, $R_b$, and $R_c$ are independently alkyl, aryl, or mixed alkyl and aryl), a pyridinium moiety, a bipyridinium moiety or an imidazolium moiety, the sulfonium atom may be part of a sulfonium moiety (—$S^+R_dR_e$ wherein $R_d$ and $R_e$ are independently alkyl, aryl, or mixed alkyl and aryl) and the phosphonium atom may be part of a phosphonium moiety (—$P^+R_fR_gR_h$ wherein $R_f$, $R_g$, and $R_h$ are independently alkyl, aryl, or mixed alkyl and aryl). In another embodiment, the pH insensitive repeat unit is a negatively charged repeat unit selected from the group consisting of repeat units containing a sulfonate (—$SO_3^-$), a phosphate (—$OPO_3^-$), or a sulfate (—$SO_4^-$).

Exemplary negatively charged pH insensitive charged repeat units include styrenesulfonic acid, 2-acrylamido-2-methyl-1-propane sulfonic acid, sulfonated lignin, ethylenesulfonic acid, methacryloxyethylsulfonic acid, sulfonated ether ether ketone, and polyphosphate. Preferred pH insensitive negatively charged polyelectrolytes include polyelectrolytes comprising a sulfonate group (—$SO_3^-$), such as poly(styrenesulfonic acid) (PSS), poly(2-acrylamido-2-methyl-1-propane sulfonic acid) (PAMPS), sulfonated poly (ether ether ketone) (SPEEK), sulfonated lignin, poly(ethylenesulfonic acid), poly(methacryloxyethylsulfonic acid), their salts, and copolymers thereof.

Exemplary positively charged pH insensitive repeat units include diallyldimethylammonium, vinylbenzyltrimethylammonium, vinylalkylammoniums, ionenes, acryloxyethyltrimethyl ammonium chloride, methacryloxy(2-hydroxy) propyltrimethyl ammonium, N-methylvinylpyridinium, other N-alkylvinyl pyridiniums, a N-aryl vinyl pyridinium, alkyl- or aryl imidazolium, sulfonium, or phosphonium. Preferred pH insensitive positively-charged polyelectrolytes comprising a quaternary ammonium group, such as poly (diallyldimethylammonium chloride) (PDADMA), poly(vinylbenzyltrimethylammonium) (PVBTA), poly(alkyammoniums), ionenes, poly(acryloxyethyltrimethyl ammonium chloride), poly(methacryloxy(2-hydroxy)propyltrimethyl ammonium chloride), and copolymers thereof; polyelectrolytes comprising a pyridinium group such as poly(N-methylvinylpyridinium) (PMVP), other poly(N-alkylvinylpyridines), and copolymers thereof.

For illustrative purposes, certain of the pH insensitive positively-charged moieties are illustrated below:

Pyridinium having the structure:

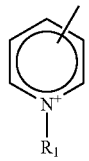

wherein $R_1$ is optionally substituted alkyl, aryl, alkaryl, alkoxy or heterocyclo. Preferably, $R_1$ is alkyl or aryl, and still more preferably $R_1$ is methyl;

Imidazolium having the structure:

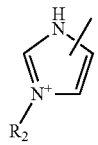

wherein $R_2$ is optionally substituted alkyl, aryl, alkaryl, alkoxy or heterocyclo. Preferably, $R_2$ is alkyl or aryl, and still more preferably $R_2$ is methyl;

Bipyridinium having the structure:

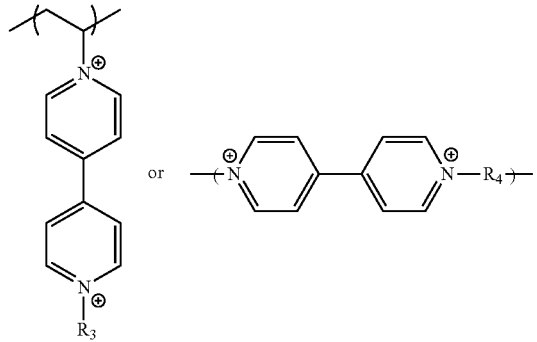

wherein $R_3$ and $R_4$ are optionally substituted alkyl, aryl, alkaryl, alkoxy or heterocyclo. Preferably, $R_3$ and $R_4$ are alkyl or aryl, and still more preferably $R_3$ is methyl.

The pH insensitive polyelectrolyte may comprise a repeat unit that contains protonatable functionality, wherein the functionality has a pKa outside the range of experimental use. For example, polysulfonic acids have pKa values between about 0 and 2. Though they may be protonated at sufficiently low pH (e.g., less than 2) they remain fully charged, and may be treated as pH-independent polyelectrolytes as long as experimental conditions remain above about pH 2. For physiological applications, which take place over the pH range of 5-8, these polysulfonates may be considered pH independent.

Preferably, the pH insensitive groups constitute about 10 mol % to about 100 mol % of the repeat units of the polyelectrolyte, more preferably from about 20 mol % to about 80 mol %. Preferably, the pH sensitive groups constitute about 30 mol % to about 70 mol % of the repeat units of the polyelectrolyte.

Optionally, the polyelectrolytes comprise an uncharged repeat unit that is not pH sensitive in the operating pH range, for example, about pH 3 to about pH 9. Said uncharged repeat unit is preferably hydrophilic. Preferred uncharged hydrophilic repeat units are acrylamide, vinyl pyrrolidone, ethylene oxide, and vinyl caprolactam. The structures of these uncharged repeat units are shown in Table II. Preferred uncharged repeat units also include N-isopropylacrylamide and propylene oxide.

TABLE II

Neutral Repeat Units

| Name | Structure |
| --- | --- |
| Acrylamide | (structure shown) |
| Vinylpyrrolidone | (structure shown) |
| Ethylene oxide | (structure shown) |
| Vinylcaprolactam | (structure shown) |

Salt Ions

According to some embodiments of the invention, the polyelectrolytes are deposited onto the exposed surface of a substrate from a polyelectrolyte solution. In some embodiments, the polyelectrolyte solution further comprises at least one dissolved salt, or comprises two or more dissolved salts. In some embodiments, the dissolved salt concentration in the polyelectrolyte solution is between about 0.01M (molar) and about 5M (molar), or between about 0.1M (molar) and about 5M (molar), such as between about 0.2M and about 4M, or between about 1M and about 4M, such as between about 2M and about 4M, or between about 0.2M and about 1M. A wide variety of salt ions may be added to the polyelectrolyte complex to dope the starting polyelectrolyte complex. In general, the salt may comprise any cation selected from among the alkali metal cations, alkaline earth metal cations, transition metal cations, semi-metallic cations, and organic cations such as amines or quaternary ammoniums. The salt(s) may comprise a mixture of two or more of any of these cations. Among the alkali metal cations, lithium, sodium, potassium, and rubidium may be incorporated into the polyelectrolyte complex, with sodium and potassium being particularly preferred. In certain physiological applications, the choice of alkali metal cations may be limited to sodium or potassium ions. Among the alkaline earth metal cations, magnesium, calcium, strontium, and barium may be incorporated into the polyelectrolyte complex. Calcium and magnesium cations are particularly preferred, and for physiological applications, the choice of alkaline earth metal cations may be limited to calcium and magnesium. A wide variety of transition metals may be incorporated into the polyelectrolyte complex including scandium, yttrium, titanium, zirconium, vanadium, niobium, chromium, molybdenum, manganese, iron, ruthenium, cobalt, rhodium, nickel, palladium, platinum, copper, silver, gold, and zinc. In certain physiological applications, the choice of transition metal cations may be limited to zinc, iron, and copper. Other metal cations that may be incorporated into the extruded articles include aluminum, indium, tin, lead, and bismuth. Organic cations that may be included include ammonium, primary, secondary, and tertiary amines, and quaternary ammoniums comprising alkyl groups having from one to eight carbon atoms. Primary amines, secondary amines, and tertiary amines are protonated to achieve positive charge and are thus pH sensitive. Exemplary primary amines, secondary amines, and tertiary amines are protonated forms of methylamine, dimethylamine, trimethyl amine, ethylamine, diethylamine, and triethylamine among others. Quaternary amines are pH insensitive groups. Exemplary quaternary amines include tetramethylammonium, tetraethylammonium, tetrapropylammonium, among others. In one embodiment, the amine is a linear polyamine such as ethylene diamine, diethylene triamine, dipropylene triamine, triethylene tetraamine, tripropylene tetraamine, tetraethylene pentaamine, tetrapropylene pentaamine, spermine, or spermidine.

The anion may be selected from among halide anions, oxoanions, and organic anions. A combination of anions may be incorporated into the polyelectrolyte complex. Halide ions that may be incorporated into the polyelectrolyte complex include fluoride, chloride, bromide, and iodide. In one preferred embodiment, the halide anion is bromide ion. Oxoanions that may be incorporated into the polyelectrolyte complex include sulfonate, sulfate, sulfite, phosphate, phosphite, phosphonate, pyrophosphate, hypochlorite, chlorite, chlorate, perchlorate, iodate, periodate, bromate, borate, carbonate, nitrate, nitrate, aluminate, and manganate, among others. Organic anions that may be incorporated into the polyelectrolyte complex include carboxylates, such as citrate, lactate, acetate, benzoate, formate, malate, malonate, fumarate, oxalate, propionate, butyrate, tartrate, and valerate, phthalate, among others. Hydrophobic anions, such as those with a high hydrocarbon to charge ratio, are preferred for enhancing doping. Preferred organic anions for physiological applications include citrate and lactate. Organic solvent is optionally added to the aqueous salt solution.

Other preferred salts include chloride salts, citrate salts, and phosphate salts. Preferred chloride salts include sodium chloride, potassium chloride, magnesium chloride, calcium chloride, and aluminum chloride. Preferred citrate salts include trisodium citrate, disodium hydrogencitrate, sodium dihydrogencitrate, tripotassium citrate, dipotassium hydrogencitrate, potassium dihydrogencitrate, magnesium citrate, and calcium citrate. Preferred phosphate salts include trisodium phosphate, disodium hydrogen phosphate, sodium dihydrogen phosphate, tripotassium phosphate, dipotassium hydrogen phosphate, potassium dihydrogen phosphate, disodium potassium phosphate, sodium dipotassium phosphate, sodium potassium hydrogen phosphate, calcium phosphate, and magnesium phosphate.

In view of the above cations and anions, a wide variety of salts may be used in the polyelectrolyte solutions according to the present invention. Preferably, the salts are soluble in aqueous solution at a concentration at least sufficient to incorporate ions into the polyelectrolyte complex starting material to an extent sufficient to achieve the doping level needed for the desired viscosity.

Deposition Methods and Substrates

While this invention employs polyelectrolyte complex thin films, a preferred method of depositing said complex is by the alternating layer-by-layer deposition method. The preferred method of alternating exposure of the substrate or material to be coated is by alternate immersion in polyelectrolyte solutions, or alternate spraying of polyelectrolyte solutions. The alternating polyelectrolyte layering method, however, does not generally result in a layered morphology of the polymers with the film. Rather, the polymeric components interdiffuse and mix on a molecular level upon incorporation into the thin film. See Lösche et al., *Macromolecules* 31, 8893 (1998). Thus, the polymeric components form a true molecular blend with intimate contact between polymers driven by the multiple electrostatic complexation between positive and negative polymer segments. The complexed polyelectrolytes within the PEMU film have similar morphology to a polyelectrolyte complex formed by mixing solutions of positive and negative polyelectrolyte. It is also known that although there is extensive intermingling of neighboring layers over a range of 4-6 nominal layers, it is possible to obtain actual layers of different composition, or strata, by interspersing several layers made from one pair of polyelectrolytes by several layers made from a different pair. See Lösche et al., *Macromolecules* 31, 8893 (1998). For example, if polymers A and C are positively charged and polymers B and D are negatively charged, about 3 or 4 pairs of A/B layers followed by about 3 or 4 pairs of A/D or C/D layers will produce two strata of distinct composition.

Alternatively, the thin film coating may be applied to a surface using a pre-formed polyelectrolyte complex. See Michaels, *Polyelectrolyte Complexes*, Ind. Eng. Chem. 57, 32-40 (1965) and Michaels (U.S. Pat. No. 3,467,604). This is accomplished by mixing the oppositely-charged polyelectrolytes to form a polyelectrolyte complex precipitate which is then dissolved or re-suspended in a suitable solvent/liquid to form a polyelectrolyte complex solution/dispersion. The polyelectrolyte complex solution/dispersion is then applied to the substrate surface and the solvent/liquid is evaporated, leaving behind a film comprising the polyelectrolyte complex. To aid in dissolution or dispersion of the complex, both a salt, such as sodium bromide, and an organic solvent, such as acetone is optionally added to the solution comprising the precipitated complex.

In some embodiments, the polyelectrolyte complex comprising the interpenetrating network of at least one predominantly positively charged polyelectrolyte and at least one negatively charged polyelectrolyte are depositing by alternating contact of a polyelectrolyte solution comprising at least one predominantly positively charged polyelectrolyte and a first salt and a polyelectrolyte solution comprising at least one predominantly negatively charged polyelectrolyte and a second salt.

In some embodiments, a first polyelectrolyte solution comprises the dissolved positively charged polyelectrolyte at a concentration between about 1% by weight and about 10% by weight and a first salt. A second polyelectrolyte solution comprises the dissolved negatively charged polyelectrolyte at a concentration between about 1% by weight and about 10% by weight and a second salt.

In some embodiments, a first polyelectrolyte solution comprises the dissolved positively charged polyelectrolyte at a concentration between about 1% by weight and about 5% by weight and a first salt. A second polyelectrolyte solution comprises the dissolved negatively charged polyelectrolyte at a concentration between about 1% by weight and about 5% by weight and a second salt.

In some embodiments, a first polyelectrolyte solution comprises the dissolved positively charged polyelectrolyte at a concentration between about 5% by weight and about 10% by weight and a first salt. A second polyelectrolyte solution comprises the dissolved negatively charged polyelectrolyte at a concentration between about 5% by weight and about 10% by weight and a second salt.

In some embodiments, the first salt and the second salt may be identical. In some embodiments, the concentrations of the first salt and the second salt may be identical.

According to some embodiments of the present invention, a positively charged polyelectrolyte and a negatively charged polyelectrolyte are loosely blended together to form a coacervate. The coacervate additionally comprises a solvent. The solvent may be selected from the group consisting of water, acetone, ethanol, methanol, trifluoroethanol, and any combination thereof. The coacervate may comprise between about 1% by weight and about 10% by weight positively charged polyelectrolyte and between about 1% by weight and about 10% by weight negatively charged polyelectrolyte. The coacervate further comprises a salt. In some embodiments the coacervate may comprise between about 1% by weight and about 5% by weight positively charged polyelectrolyte and between about 1% by weight and about 5% by weight negatively charged polyelectrolyte. In some embodiments, the coacervate may comprise between about 5% by weight and about 10% by weight positively charged polyelectrolyte and between about 5% by weight and about 10% by weight negatively charged polyelectrolyte.

Optionally, the PECTF is deposited as a polyelectrolyte coacervate which is a liquid like form of polyelectrolyte complex. Coacervates are made from complexes by the addition of sufficient salt. In fact, coacervates are simply highly-doped complexes. The ion pairs between polyelectrolytes have been minimized, but not eliminated, by the addition of enough salt. A polyelectrolyte coacervate is a viscous liquid, with some elasticity, which may be applied to a surface by any method known to the coatings art such as doctor blading, painting, spraying, rod coating, web coating, dip coating, brush-on, spin coating and coating with rollers. Following deposition of the coacervate, the viscous film is washed in solvent to remove salt and to harden the PECTF. The surface of the PECTF is then modified by the preferred method to have the desired net negative fixed charge density.

In some embodiments, the layer or coating is deposited upon a substrate comprising an exposed surface, wherein the exposed surface of the substrate is in contact with the back surface region of the layer or coating suitable for culturing quasispherical cell clusters. In some embodiments, the substrate comprises a solid support comprising a material selected from the group plastic, metal, ceramic, and gel. Suitable plastics include but are not limited to polycarbonate, poly(methyl methacrylate), polystyrene, poly(ethylene terephthalate), polysulfone, polyamide, polyurethane, polyethylene, polypropylene. Suitable metals include, but are not limited to steel, titanium and nickel alloys. Suitable ceramics include titanium dioxide, cerium oxides, alumina, silica and glass. Suitable gels include those that are preferably cross-linked, such as acrylamides, sepharose, and alginate.

In one embodiment of this invention, the polyelectrolyte complex is formed on an exposed surface of a polymer or plastic substrate. Polyelectrolyte complexes, especially those formed by the layer-by-layer alternating deposition technique, are known by those skilled in the art to adhere to plastic materials. For example, Chen and McCarthy (*Macromolecules,* 30, 78 (1997) describe the layer-by-layer deposition of polyelectrolyte complex on poly(ethylene terephthalate). Even fluorinated polymers, such as Dupont's Teflon™, are known to be coated by polyelectrolyte complex using the layer-by-layer technique (see Hsieh et al. *Macromolecules,* 30, 8453 (1997). Barker et al. (*Anal. Chem.,* 72, 5925 (2000)) (See also Locascio et al. U.S. Pat.

Pub. No. 2002/0053514) have disclosed the layer-by-layer deposition of polyelectrolytes on plastic microfluidic channels. Thus, preferred plastic substrates on which PECTFs may be formed include polycarbonate, poly(methyl methacrylate), polystyrene, poly(ethylene terephthalate), polysulfone, or polyamide, with the proviso that solvents used to process the polyelectrolyte complex thin film does not attack the substrate on which the thin film of complex is being formed.

The geometry of the substrate on which the PECTF is deposited is preferably selected to encourage interactions and encounters of cells with each other. Thus, the surface of the substrate may be curved, dished or dimpled (like a golf ball) to encourage said interactions. The surface may comprise wells with sloped sidewalls. Under the influence of gravity cells come together to form clusters. Although cluster formation is observed on flat substrates, such geometries accelerate cell encounters.

For the purposes of this invention, the PECTF is preferably ultrathin, less than 1000 nm thick, more preferably less than 100 nm thick. In some embodiments, the PECTF is at least about 0.1 nm thick, such as at least about 1 nm thick. It has been found that thinner films induce the desired quasispherical cluster. For example, a PEMU of PSS and PDADMA, grown from 0.1 M NaCl was thinner than one grown from 1.0M NaCl. The thinner PEMU was effective at inducing cell clustering.

For fast throughput and coating of surfaces, one method of applying the polyelectrolyte complex is by spraying of a surface. Spraying is especially preferred when applying the coating to large areas using alternating exposure of oppositely-charged polyelectrolyte solutions. Spraying alternating oppositely-charged polyelectrolyte solutions has several advantages over the Michaels coating and evaporation method, including: improved control over film thickness especially the ability to make extremely thin films (e.g., less than about 1 μm), and enhanced uniformity of film thickness especially over uneven surfaces and contours. The solutions may be sprayed onto a substrate by any applicable means (e.g., an atomizer, an aspirator, ultrasonic vapor generator, entrainment in compressed gas, or inkjet sprayer). In fact, a hand operated "plant mister" has been used to spray the polyelectrolyte solutions. Typically, the droplet size in the spray is about 10 nm to about 1 mm in diameter. Preferably, the droplet size is about 10 μm to 100 μm in diameter. The coverage of the spray is typically about 0.001 to 1 mL/cm$^2$, and preferably about 0.01 to 0.1 mL/cm$^2$.

In order to create a pattern of polyelectrolyte on a surface, spraying is preferably done though a mask which defines the pattern. In some embodiments, spraying employs any spraying technique known to the art such as spraying using compressed air, entrainment of the liquid by spraying using a carrier gas, ultrasonic spraying, or misting. Preferably, spraying through a mask is performed with a fine spray, such as that produced by ultrasonic vaporization. The mask is preferably placed on or near the surface to be coated. Many patterns of different levels of complexity are possible. Preferred dimensions for features on the mask range from about 10 micrometers to several centimeters. The duration in which the polyelectrolyte solution is typically in contact with the surface it is sprayed upon (i.e., the contact time) varies from seconds to several minutes to achieve a maximum, or steady-state, thickness. The contact duration is selected based on the desired relationship between throughput (i.e., the rate at which alternating layers are created) and layer thickness. Specifically, decreasing the contact duration increases throughput and decreases layer thickness whereas increasing the duration decreases throughput and increases thickness. Preferably, the contact time is selected to maximize the throughput of layers that have a satisfactory thickness and are uniform across the surface.

Other preferred methods of depositing the polyelectrolyte solutions and/or polyelectrolyte complex include casting, dip coating, spin coating and doctor blading. Particularly preferred methods are dip coating and spraying.

Optionally, rinsing may be employed to remove non-adsorbed polyelectrolyte between the application of each polyelectrolyte solution. The rinsing liquid comprises an appropriate solvent (e.g., water or organic solvent such as alcohol). For water-soluble polyelectrolytes the preferred solvent is water. If the solvent is water, the rinsing liquid may also comprise an organic modifier (e.g., ethanol, methanol, or propanol). The concentration of organic modifier can be as high as less than 100 percent by weight of the rinsing liquid, but is preferably less than about 50 percent by weight. The rinsing liquid may also comprise a salt (e.g., sodium chloride) which is soluble in the solvent and the organic modifier, if included in the rinsing liquid. The concentration of salt is preferably below about 10 percent by weight of the rinsing liquid. It should be noted that as the concentration of organic modifier increases the maximum solubility concentration of salt decreases. The rinsing liquid, however, should not comprise a polyelectrolyte. The rinsing step may be accomplished by any appropriate means (e.g., flushing, dipping, or spraying). For spray rinsing, the amount of waste is preferably reduced by recycling the polymer solutions removed from the surface. Optionally, prior to depositing the second through nth layer of sprayed oppositely charged polyelectrolyte solution, the surface of the multilayer structure may be dried.

When performing multilayering by dipping, in order to avoid precipitation through cross-contamination, at least one of the rinse steps preferably employs a solvent which mixes with the solvents in which the polyelectrolytes are dissolved/dispersed.

Adsorption of molecules on surfaces is driven by the net influence of various interdependent interactions between and within surfaces and biopolymer. Possible polyelectrolyte interactions can arise from 1) van der Waals forces 2) dipolar or hydrogen bonds 3) electrostatic forces 4) hydrophobic effects. Given the apparent range and strength of electrostatic forces, it is generally accepted that the surface charge plays a major role in adsorption. However, adsorbers such as proteins are remarkably tenacious, due to the other interaction mechanisms at their disposal. It is an object of this invention to show how surfaces may be selected to encourage the formation of quasispherical cell clusters.

Polyelectrolyte complexes comprising zwitterions useful for preventing protein and/or cell adhesion have been described in U.S. Publication No. 2005/0287111, which is hereby incorporated by reference as if set forth in its entirety. It has been found that polymers comprising zwitterionic functional groups alone do not form polyelectrolyte complexes if they are employed under conditions that maintain their zwitterionic character. This is because the charges on zwitterionic groups do not exhibit intermolecular interactions. Therefore, preferred polymers comprising zwitterionic groups also comprise additional groups capable of intermolecular interactions, such as hydrogen bonding or ion pairing. More preferably, polyelectrolytes comprising zwitterionic groups also comprise charged groups that are not zwitterionic. Zwitterionic groups are present on polyelectrolytes as blocks or randomly dispersed throughout the polymer chain. Preferably, polyelectrolytes comprise between about 1% and about 90% zwitterions units, and more preferably said polyelectrolyte comprises between about 10% and about 70% zwitterionic units. Preferred compositions of polyelectrolytes comprising zwitterionic repeat units also comprise between about 10% and about 90% non-zwitterionic charged repeat units. Preferred zwitterionic repeat units are poly(3-[2-(acrylamido)-ethyldimethyl ammonio]propane sulfonate) (PAEDAPS) and poly(N-propane sulfonate-2-vinyl pyridine) (P2PSVP). The structures of these zwitterions are shown in Table III. Examples of other suitable zwitterionic groups are described in U.S. Publication No. 2005/0287111.

TABLE III

Zwitterionic Repeat Units

| Name | Structure |
| --- | --- |
| 3-[2-(acrylamido)-ethyldimethyl ammonio] propane sulfonate (AEDAPS) | 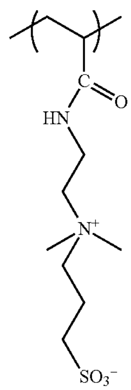 |
| N-propane sulfonate-2-vinyl pyridine (2PSVP) | 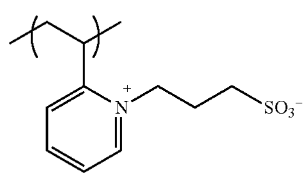 |

It has been disclosed (U.S. Publication No. 2005/0287111) that films of polyelectrolyte complex prepared by the multilayering method are able to control the adsorption of protein. It is also generally known by those skilled in the art that hydrophilic units, such as ethylene oxide (or ethylene glycol), are effective in reducing the overall propensity of biological macromolecules, or biomacromolecules, to adsorb to surfaces (see Harris, *Poly(ethylene glycol) Chemistry: Biotechnical and Biomedical Applications*, Plenum Press, New York, 1992). Yang and Sundberg (U.S. Pat. No. 6,660,367) disclose materials comprising ethylene glycol units that are effective at resisting the adsorption of hydrophilic proteins in microfluidic devices. The ethylene oxide (or ethylene glycol) repeat units are preferably present as blocks within a block copolymer. Preferably, the block copolymer also comprises blocks of charged repeat units, allowing the material to be incorporated into a PECTF. Sufficient ethylene oxide repeat units are required to promote resistance to protein adsorption, but too many ethylene oxide units do not allow polyelectrolyte complexes to associate. Therefore, the preferred mole ratio of charged to neutral repeat units in a PECTF is from 10:1 to 1:4, and a more preferred ratio is 5:1 to 1:2.

Ethylene oxide repeat units may also be employed in comb polymers, preferably with a main, charged chain comprising a plurality of at least one of the charged repeat units listed previously and oligomers or polymers of ethylene oxide units grafted to this main chain. Such an architecture is termed a comb polymer, where the charged backbone represents that backbone of the comb and the grafted ethylene oxide oligomers or polymers represent the teeth of the comb.

Preferably the location of the zwitterionic and/or polyethylene oxide repeat units is at the surface of the PECTF. In order to place said zwitterionic and/or polyethylene oxide repeat units at the surface of the PECTF the zwitterionic and/or polyethylene oxide repeat units are sorbed on the coating after it is deposited, for example by exposing the article coated with PECTF to a solution comprising a polyelectrolyte comprising zwitterionic or ethylene oxide repeat units. Alternatively, the zwitterionic or ethylene oxide functionality can be chemically grafted to the surface of the PECTF using chemical grafting or coupling methods.

In one preferred embodiment, chemical crosslinking is introduced into the polyelectrolyte complex thin film for stability. After applying the PECTF, it may be treated with a difunctional crosslinking agent, such as $XCH_2\text{-}\varphi\text{-}CH_2X$, where X is a halogen (Cl, Br, or I) and $\varphi$ is a phenyl group. The phenyl group may be replaced by another aromatic or aliphatic moiety, and easily-diplaceable groups, such as toluene sulfonate, may replace the halogen. A preferred crosslinking agent is a dihalogenated compound, such as an aromatic or aliphatic dibromide, which is able to alkylate residual unalkylated units on two adjoining polyelectrolyte chains.

Another preferred method of chemical crosslinking a PECTF is heat treatment. For example, Dai et al. (*Langmuir* 17, 931 (2001)) disclose a method of forming amide crosslinks by heating a polyelectrolyte multilayer comprising amine and carboxylic acid groups. Yet another preferred method of introducing crosslinking, disclosed by Kozlovskaya et al. (Macromolecules, 36, 8590 (2003)) is by the addition of a carbodiimide, which activates chemical crosslinking. The level of chemical crosslinking is preferably 0.01% to 50%, and more preferably 0.1% to 10%.

Another method of chemical crosslinking of a polyelectrolyte complex is by photocrosslinking. Photocrosslinking may be achieved by the light-induced decomposition or transformation of functional groups, such as diarylbenzophenones, that form part of the polymer molecules. See, for example, Strehmel, Veronika, "Epoxies: Structures, Photoinduced Cross-linking, Network Properties, and Applications"; Handbook of Photochemistry and Photobiology (2003), 2, 1-110. See also Allen, Norman S., "Polymer photochemistry", Photochemistry (2004), 35, 206-271; Timpe, Hans-Joachim "Polymer photochemistry and photocrosslinking" Desk Reference of Functional Polymers (1997), 273-291, and Smets, G., "Photocrosslinkable polymers", Journal of Macromolecular Science, Chemistry (1984), A21 (13-14), 1695-703. Alternatively, photocrosslinking of a PECTF may be accomplished by infusing the PECTF with a small photoactive crosslinker molecule, such as diazidostilbene, then exposing the polyelectrolyte complex to light.

In some embodiments, the polyelectrolyte complex comprises further physical crosslinks created by hydrogen bonding. Hydrogen bonding is weaker than chemical bonding and occurs between a hydrogen bond donor and a hydrogen bond acceptor. Hydrogen bonds are minimally impacted by the presence of salt and thus the level of physical crosslinking due to hydrogen bonding remains substantially the same as the salt concentration is varied. Accordingly, the polyelectrolyte complex capsules further comprise polymer repeat units capable of hydrogen bonding. Examples of hydrogen bond donor/acceptor pairs are presented in U.S. Pat. Nos. 6,740,409 and 7,470,449 as well as U.S. Publication No. 2005/0163714, each of which is hereby incorporated by reference as if set forth in their entireties.

For physiological applications of the PECTF other additives may be added during the method of the present invention. For example, articles comprising the PECTF that are to be implanted in vivo may optionally further comprise antibacterial and/or anti-inflammation and/or antirejection agents and/or growth factors. These additives respectively aid in reducing infection, inflammation or rejection of the implanted article and encouraging tissue proliferation. Examples of antibiotics are well known to the art and are to be found in E. M. Scholar, The Antimicrobial Drugs, New York, Oxford University Press, 2000 or the Gilbert et al., The Stanford Guide to Antimicrobial Therapy, Hyde Park, V T, 2000, or the R. Reese, Handbook of Antibiotics, Philadelphia, Lippincot, 2000. Antibacterial agents include silver including silver nanoparticles. Other additives are known to the art for promoting various biomedical properties. These include paclitaxel, seratonin, heparin, and anticlotting factors. Unlike additives used to modify the physical properties of the PECTF, additives with biological or biomedical activity are typically added in lower concentration. Accordingly, such additives preferably comprise between 0.0001% (1 μg/g) and 5% by weight of the polyelectrolyte complex article. The concentration of the additive is typically adjusted to obtain the optimum physiological response.

Additives providing biological or bioactive properties are either mixed with one of the constituent polyelectrolyte solutions before PECTF is prepared or they are sorbed into the surface of the complex after the PECTF is formed.

A fluorinated polyelectrolyte multilayer, on which smooth muscle cells were grown, has been described in U.S. Pub. No. 2005/0287111, which is herein incorporated by reference. This multilayer comprised fluorinated polyelectrolyte complex, on which cells grow. However, the cells do not consume the fluorinated material. In one aspect of the present invention, therefore, the PECTF further comprises an external surface stratum of fluorinated polyelectrolyte. The surface stratum is preferably obtained by immersing the PECTF in a solution of fluorinated polyelectrolyte. The process may be repeated with alternating positive and negative fluorinated polyelectrolytes to obtain a thicker surface stratum.

The preferred morphology for cell culture in the present invention is a cluster approximating a sphere, or "quasispherical." A quasispherical shape is any rounded shape, such as a sphere, a tri-axial ellipsoid, an oblate ellipsoid, or a prolate ellipsoid. In some preferred embodiments, in a quasisphere, the aspect ratio between any two dimensions measured across the sphere is less than 2. For example, a cluster the shape of a potato may be quasispherical as long as the ratio of length to width is less than 2. The non-preferred morphology is a flattened aggregate or clump of cells on the surface. The preferred morphology may be identified by microscopic examination of the cell culture. Quasispherical clusters interact minimally with the surface and may roll if the substrate is moved. Undesired clumps or aggregates of cells are probably attached to the surface and are identified by the absence of overhang between the aggregate and the surface.

The preferred sphere morphology comprises a cluster of at least 2 cells in contact. The sphere may be irregular on the micrometer scale especially if fewer than about 5 cells are aggregated. Irregularities are caused by cell membrane tensions which resist the distortion required to form a perfect sphere. The sphere morphology indicates preferred interaction of cells with themselves as opposed to interactions with the surface. However, complete lack of interaction with the surface, as induced by the zwitterions surface described in, for example, U.S. Pub. No. 2005/0287111, is not required. In fact, the examples below describe how live cell imaging of quasispherical clusters on the preferred surfaces reveal probing of, and weak interactions with, the surface by the cluster.

As stated above, a quasispherical cluster of cells is advantageous for certain types of cell culture, such as stem cells, which must remain undifferentiated while they are multiplied (expanded). At some point, under the influence of chemical and/or physical cues, stem cells differentiate into the desired cell line. While cells have been seen to be partially aggregated on many PECTFs the quasispherical cluster morphology has not been observed and was unanticipated. The Examples below show how this unusual quasispherical cluster morphology is not correlated to surface roughness.

With all cell growth a medium is selected to provide the proper environment. Compositions of cell growth media are multicomponent and vary widely, especially media comprising a fluid that has been derived from a biological source (such as serum). In the present invention, the medium is preferably selected to lead to the preferred quasispherical cell morphology on the preferred surface. Media selection is done experimentally for each cell type with optimal results judged as the preferred morphology obtained on the preferred surface.

As-made PECTFs could not induce the quasispherical clustering. Only following additional treatments with polyelectrolyte were cells observed to form said clusters. After extensive evaluation of the PECTFs it was discovered that a higher net negative fixed surface charge, than that resulting from multilayering was required to induce the formation of quasispherical clusters. The additional negative fixed surface charge was created by additional treatment of the as-made PECTF. Said treatment comprised additional contact of the PECTF in solutions of negative polyelectrolyte comprising a salt. As a result of said additional contact the negative fixed surface charge density of the PECTF increases.

The additional negative fixed surface charge is preferably added to the PECTF using a conditioning solution comprising net negative polyelectrolyte in a concentration of a conditioning salt that is higher than the salt concentration used to deposit the PECTF. For example, if the PECTF is deposited from a solution comprising 0.1M NaCl, the additional negative fixed surface charge is added from a conditioning solution comprising negative polyelectrolyte and a conditioning salt, optionally the same NaCl salt, at a concentration of at least about 0.2 M, such as at least about 0.5 M, or even at a concentration of at least about 1.0M. The concentration of the conditioning salt in the condition solution from which additional negative polyelectrolyte is added is preferably at least twice that of the concentration of salt from which the PECTF was deposited on a molar basis, such as at least about four times the concentration on a molar basis, at least about five times the concentration on a molar basis, or at least about ten times the concentration on a molar basis.

In the preferred surface treatment, a PECTF of thickness less than 100 nm is exposed to an aqueous solution comprising a surface predominantly negatively charged polyelectrolyte and a salt (i.e., a conditioning salt in order to differentiate it from the first salt and second salt of the polyelectrolyte solutions discussed previously). In some embodiments, the concentration of the surface predominantly negatively charged polyelectrolyte is preferably at a higher concentration than the polyelectrolytes in the polyelectrolyte solutions used for depositing the PECTF on the substrate. The PECTF is allowed to remain in contact with said aqueous solution for a fixed time, preferably the minimum time required for the additional surface predominantly negatively charged polyelectrolyte to add to the surface to give the preferred net fixed surface charge. Typically, this time is on the order of minutes.

Optionally, the PECTF may be heated during the preferred surface treatment. The heat treatment accelerates the addition of net negative polyelectrolyte. Preferably the PECTF is not heated beyond its glass transition temperature to avoid excessive addition of negative polyelectrolyte and to maintain the net surface fixed charge density below its preferred upper limit.

In some embodiments, the surface predominantly negatively charged polyelectrolyte is deposited from a conditioning polyelectrolyte solution comprising a conditioning salt, and the concentration of the conditioning salt is higher than the concentration of the first salt in the polyelectrolyte solution used to deposit the predominantly positively charged polymer in the PECTF. In some embodiments, the surface predominantly negatively charged polyelectrolyte is deposited from a conditioning polyelectrolyte solution comprising a conditioning salt, and the concentration of the conditioning salt is higher than the concentration of the second salt in the polyelectrolyte solution used to deposit the predominantly negatively charged polymer in the PECTF. In some embodiments, the concentration of the conditioning salt is higher than the concentration of both the first salt and the second salt in their respective solutions used to build the PECTF. The concentration of the conditioning salt in the condition solution from which additional negative polyelectrolyte is added is preferably at least twice that of the concentration of the first salt and the second salt, such as at least about four times the concentration on a molar basis, at least about five times the concentration on a molar basis, or at least about ten times the concentration on a molar basis.

Instead of using a higher concentration of the same salt to add negative polyelectrolyte to the surface of the PECTF, a salt, of equal or greater concentration, comprising ion(s) that are different than those used to construct the PECTF may be employed. These ions are selected according to their rank in the Hofmeister series. The Hofmeister series or lyotropic series is a classification of ions in order of their ability to salt out or salt in proteins. Anions appear to have a larger effect than cations, and are usually ordered:

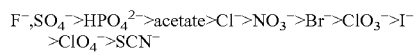

The order of cations is usually given as

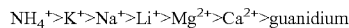

The ions in the Hofmeister series, from left to right above, decrease in ability to augment surface tension and increase in ability to dissolve proteins. For example, if 0.1M NaCl is employed in the construction of the PECTF, the salt used for subsequent addition of negative polyelectrolyte may comprise 0.1M $NaClO_4$. Mixtures of salts are also suitable for this invention. Examples of salts are given above.

The surface charge is defined as the net fixed electrical charge at the surface or within 1 nm of the surface. For example, if the surface comprises more negative polyelectrolyte than positive polyelectrolyte the net fixed electrical charge is negative. This charge is balanced by counterions to give net total charge neutrality but the counterions are mobile and not fixed and are thus free to exchange with other counterions. The density of net fixed charge is given as units of charge per unit area, for example moles of charge per $cm^2$ or moles per $m^2$ or numbers of charges per $cm^2$.

The surface charge density in this invention is the net fixed electrical charge density or the surface density of charges with exchangeable counterions. For example, a PECTF surface might comprise a surface of PSS and PDADMA comprising a net negative fixed surface charge density of $1 \times 10^{-6}$ moles per $m^2$ or 1 micromol $m^{-2}$. In other words, at the surface there is an excess of 1 micromol $m^{-2}$ of styrene sulfonate repeat units. These sulfonate units will be balanced by 1 micromol $m^{-2}$ of cations, e.g., sodium ions if the PECTF is immersed in NaCl.

Methods exist to determine said net fixed electrical charge density quickly and accurately. For example, surface-sensitive analytical techniques such as X-ray fluorescence spectroscopy (XPS) are able to measure the counterions that signal surface charge excess of one polyelectrolyte over another. However, it has been discovered that certain ions access only the surface of the PECTF and do not enter the bulk. For example, it has been discovered that tetraethylammonium ions will balance excess polyanion charge only at the surface of a PSS/PDADMA multilayer. In contrast, sodium ions and chloride ions will diffuse through the bulk of the PEMU (see for example Ghostine et al. J. Am. Chem. Soc, 135, 7636-7646 (2013)). Accordingly, as shown below, it is possible to identify the negative fixed surface charge excess by exchanging all sodium ions at the surface of a PECTF with radioactive (14-C) tetraethylammonium (TEA) ions. The amount of $^{14}$C-TEA is then measured with excellent sensitivity and accuracy using scintillation counting. This amount is then converted to moles per $m^2$.

In some embodiments, the polyelectrolyte complex thin film, PECTF, is in the form of a layer, or a coating on a substrate. In some embodiments, the polyelectrolyte complex thin film, PECTF, is in the form of a layer suitable for culturing quasispherical cell clusters. The layer comprises a bulk region comprising an interpenetrating network of at least one predominantly positively charged polyelectrolyte and at least one predominantly negatively charged positive polyelectrolyte, a back surface region, and a front surface region. A PECTF surface, e.g., back surface and/or front surface might comprise a surface of a predominantly positively charged polyelectrolyte, a predominantly negatively charged polyelectrolyte, or both a predominantly positively charged polyelectrolyte and a predominantly negatively charged polyelectrolyte.

In some embodiments, the front surface region comprises a net negative fixed surface charge density of between about 0.4 micromole per $m^2$ and about 1.5 micromole per $m^2$. In some embodiments, the front surface region comprises a net negative fixed surface charge density of between about 0.6 micromole per $m^2$ and about 1.5 micromole per $m^2$. In accord with the present invention the preferred values of negative fixed surface charge are between about 0.5 micromole per $m^2$ and about 1.5 micromole per $m^2$, such as between about 0.5 micromole per $m^2$ and about 1.0 micromole per $m^2$. More preferably the negative fixed surface charge is between about 0.6 micromole per $m^2$ and about 1.0 micromole per $m^2$.

In some embodiments, the layer or coating thickness is less than about 1000 nanometers, such as less than about 400 nanometers, or even less than about 100 nanometers. The minimum thickness may be about 1 nanometer, such as at least about 10 nanometers, or even at least about 25 nanometers.

From a fundamental standpoint, with reference to the literature on surface terminated with zwitterions, which have a net surface charge approaching zero, it would be predicted that a PECTF approaching zero should be more effective at inducing cells to cluster. As seen in the examples below, a certain amount of undesired clumping of cells is observed on as-made, low charge density PECTFs with PSS on top. In fact, for unknown reasons, a minimum amount of surface negative charge is required to induce the desired quasi-spherical cluster formation.

Without being held to a particular theory, it is believed that this amount of charge is low enough to prevent irreversible adsorption of positive protein to the surface and high enough to stop irreversible adsorption of negative protein to a surface.

EXAMPLES

For clarity, the following shorthand for multilayers is used: $(A/B)_x$ where A is the starting polyelectrolyte contacting the substrate, B is the terminating polyelectrolyte in contact with subsequent cell solutions and x is the number of layer pairs. In $(A/B)_xA$, A would be the terminating polymer. Salt, MY (cation M and anion Y), has an important role in the buildup process and is represented by $(A/B)_x$ @c MY, where c is the molarity of the salt (MY) in the polymer solution. The pH can be included in the nomenclature especially when using pH dependent PEMUs. For example, $(PAH/PAA)_2$ @0.25 M NaCl @pH 7.4, represent two pairs of PAH/PAA built at 0.25 M NaCl and a pH of 7.4.

The following non-limiting examples are provided to further illustrate the present invention.

Materials.

Poly(4-styrenesulfonic acid) (PSS; 18 wt % in water, molar mass ~75,000 g mol$^{-1}$), poly(diallyldimethylammonium chloride) (PDADMAC; 20 wt % in water, molar mass 400,000-500,000 g mol$^{-1}$), and sodium chloride (99.5%) were used as received from Sigma-Aldrich. All solutions were prepared using 18MΩ deionized water (Barnstead, E-pure). Polyelectrolyte Solutions. PSS and PDADMAC were 10 mM (based on the monomer repeat unit) polymer solutions with a [NaCl] of 0.15M or 1.0M. The pH of the solutions was adjusted to pH ca. 7 with 1.0M NaOH.

Example 1. Polyelectrolyte Multilayer, PEMU, Buildup

[PDADMA/PSS, x]$_n$ multilayers, examples of PECTF, were built manually at room temperature using a layer-by-layer assembly on square pieces of polished silicon (Si 100), where "n" indicates the number of bilayers and x represents the NaCl concentration used for the buildup. For example [PDADMA/PSS, 1.0]$_{10}$[PDADMA, 1.0] indicates 20 alternating layers of PDADMA and PSS, starting with PDADMA on the Si wafer, using 1.0 M NaCl, terminated with a layer of PDADMA in 1.0 M NaCl. 20-layer PEMUs prepared with 0.15M NaCl had a thickness of around 40 nm, while films prepared with 1.0M NaCl had a thickness of around 400 nm.

Si wafers were cleaned by immersion, for 10 min, in "piranha" solution (70:30 mixture of sulfuric acid and hydrogen peroxide). Wafers were then rinsed with deionized water and dried with a stream of $N_2$. The buildup of the PEMUs was done manually using 1000 mL beakers and a holder with a capacity for 6 wafers. The dipping time in each 10 mM polyelectrolyte solution was 5 minutes followed by three consecutive water rinses for 1 minute, after which the PEMU was air-dried. For cell culture experiments, PEMUs were built on flat bottom, polystyrene 6- or 12-well plates (Jet-Biofil, Tissue Culture Products) instead of silicon wafers using the same procedure.

Example 2. Cell Culture

3T3-Swiss albino fibroblasts (initially purchased from American Type Culture Collection as ATCC CCL-92 cells and maintained in the lab for numerous generations) were cultured in Dulbecco's Modified Eagle's Medium supplemented with 1 g L$^{-1}$ L-glutamine, 1.2 g L$^{-1}$ sodium bicarbonate (Sigma-Aldrich), 10% Cosmic Calf Serum (Thermo Scientific), 100 U mL$^{-1}$ penicillin G, 100 μg mL$^{-1}$ streptomycin, 0.25 μg mL$^{-1}$ amphotericin B and 10 μg mL$^{-1}$ gentamicin (Invitrogen). Cells were incubated at 37° C. with 5% $CO_2$ (Nu-4750, NuAire). Uncoated 6- or 12-well plates were used as controls

Example 3. Microscopy and Live Cell Imaging

Fixed cell images were collected using a Nikon TS100 microscope fitted with a Nikon DS-Ril camera. Live cells were imaged with a Nikon Ti-E inverted microscope and a Cool Snap HQ2 camera. Cells were housed in a LiveCell chamber (Pathology Devices), incubated at 37° C. and monitored for 72 hours in 5% $CO_2$. 60% relative humidity was used to reduce media evaporation.

Example 4. Radioactive Ion Assays $^{22}$Na$^+$ (0.10 mCi, 22-Na, γ-emitter, $E_{max}$=511 keV, 1.28 MeV, half life 950 days) from Perkin Elmer was supplied as $^{22}$NaCl with an initial specific activity of 633 Ci g$^{-1}$. 1.0 mL of deionized water was added to the radiolabeled salt to make the stock solution. A 1.0×10$^{-4}$ M solution of $^{22}$NaCl with a specific activity of 5 Ci mol$^{-1}$ was prepared as follows: 255 μL of the stock solution of $^{22}$NaCl ("hot") were added to a plastic container with 50 mL of unlabeled ("cold") 1.0×10$^{-4}$ M NaCl. The specific activity of $^{22}$Na$^+$ was so high that the spike of radioactive material does not influence the overall [NaCl].

$^{125}$I$^-$ (0.79 mCi at the time of use, but initially supplied as 1.1 mCi, 125-I, γ-emitter, $E_{max}$=35 keV, half life 59.4 d) from Perkin Elmer was supplied as Na$^{125}$I with an initial specific activity of 2160 Ci mol$^{-1}$ and dissolved in 500 μL deionized water to create a stock solution. 126 μL of this stock solution of was mixed with 49.9 mL cold 1.0 mM solution of NaI. The resulting solution had a concentration of 1.0 mM Na$^{125}$I and specific activity of around 2 Ci mol$^{-1}$.

$^{14}$C-tetraethylammonium bromide (0.25 mCi, 14-C, β-emitter, $E_{max}$=156.5 keV, half life 5730 years), TEABr, supplied with a specific activity of 3.5 Ci mol$^{-1}$, was obtained from Perkin Elmer radiopharmaceuticals in 2.5 mL ethanol. This solution was used as stock. 175 μL of stock solution was added to 49.8 mL water to prepare 50 mL of 1.0×10$^{-4}$ M TEA. Because no unlabeled or "cold" TEABr was needed to reach the desired concentration, the concentration of $^{14}$C-TEABr, nominally 1.0×10$^{-4}$ M, was checked by measuring its conductivity with a conductivity meter (Thermo Scientific, Orion 3 Star) fitted with a miniature Pt conductivity probe. The conductivity was 5% higher than a 1.0×10$^{-4}$ M TEABr standard solution. The actual concentration of $^{14}$C-TEABr was 1.05×10$^{-4}$ M.

Total ion charge was obtained by exchanging with either $^{22}Na^+$ (to quantify total negative extrinsic sites) or $^{125}I$ (for total positive extrinsic sites). First, the PEMU was immersed into 5 mL of radiolabeled ion (specific activity ca. 5 Ci mol$^{-1}$ for $^{22}Na^+$ or 2 Ci mol$^{-1}$ for $^{125}I^-$) for 30 min. Multilayers were then removed from solution and then blown dry with a strong stream of nitrogen to remove the liquid film wetting the multilayer. The dry PEMU with radiolabeled counterions was placed face down onto a piece of plastic scintillator (SCSN-81 Kuraray, 3 mm thick, 38 mm diameter, emission peak 437 nm), which rested on the end window of a RCA 8850 photomultiplier tube, PMT, inside a dark box. A drop of immersion oil ensured good optical contact between the scintillator and the PMT window. The PMT was biased to −2300V by a Bertran 313B power supply and connected to a Phillips PM6654C frequency counter/timer. Labview software was used to collect the counts using a gate time of 10 s and a pulse threshold of −20 mV. Counts are reported as counts per second (cps). The background, subtracted from all readings, was typically 6 cps. Negative fixed surface charge was measured the same way using 0.1 mM $^{14}C$-TEABr. The respective counting efficiencies for $^{14}C$ $^{22}Na^+$ and $^{125}I^-$ were 64%, 76% and 13%.

Calibration curves (cps vs. number of moles of ion) were constructed by drying 1.0 to 5.0 µL droplets of the radiolabeled solution between Si wafers and the scintillator (Supporting Information). The nmoles obtained were converted to µmoles m$^{-2}$ using the area of the multilayer. The $N_2$ jet technique for removing the film of solution was checked by depositing one layer of PDADMA on the Si wafer and exposing it to $^{14}C$-TEABr as above. The small residual amount of isotope (0.2 µmoles m$^{-2}$), demonstrating the efficiency of the removal of solution from the Si wafer surface, was subtracted from all ion quantities.

Example 5. Atomic Force Microscopy Measurements and Imaging

Topography and thickness of the multilayers in wet (sample and tip submerged in 0.15M NaCl phosphate buffered solution) and dry (ambient air) conditions were determined using a MFP-3D AFM equipped with an ARC2 controller (Asylum Research). All AFM experiments were performed using Veeco NCHV tips with a spring constant between 20 and 80 N m$^{-1}$. The scan rate was 0.5 Hz. For dry conditions the spring constant was calibrated in air using the thermal fluctuation technique while the cantilever was tuned to 10% below the resonance frequency. For wet conditions the spring constant was calculated using the same technique while the tip was submerged in buffer solution. Tapping mode was used to obtain 10 µm×10 µm images. Topography images and rms roughness were analyzed using Igor Pro software. Multilayer thickness was measured by scanning a profile across a scratch in the multilayer.

Example 6. X-ray Photoelectron Spectroscopy

XPS measurements were made using a Perkin Elmer 5100 PHI instrument, with a non-collimated Mg K$_\alpha$ X-ray source (hv=1253.6 eV). The system was operated at a base pressure of 1.9×10$^{-8}$ torr and a take-off angle of 45°, with a pass energy set as 89.45 eV and a speed of 0.5 eV s$^{-1}$. Ten scans were averaged and quantified using database 71 software from NIST.

Example 7. FTIR Spectroscopy

IR spectra were collected with a ThermoNicolet Nexus 470 FTIR at 4 cm$^{-1}$ resolution using a MCT liquid $N_2$ cooled detector. Multilayers were prepared on double-side-polished Si wafers. These were immersed for 30 min at room temperature in 1.0 mg mL$^{-1}$ BSA in pH 7.4 phosphate buffered saline (PBS, 0.15 M NaCl), then rinsed in PBS, water and dried. The background for each spectrum was the multilayer on the Si wafer while the sample was adsorbed protein. 1000 scans were co-added.

Example 8. Live/Dead Cell Double Staining

Cell viability on surfaces was measured using a double staining kit (EMD Chemicals, Calbiochem). Fibroblasts were plated at 1.5×10$^5$ cells per well into coated 6-well plates and cultured for three days. On the third day, cell media was removed and attached cells were exposed to the double staining kit following the protocol for adherent cells recommended by the manufacturer. The Live/Dead kit is composed of two fluorescent dyes: Cyto-dye (green, excitation/emission 488 nm/518 nm) and propidium iodide (red, excitation/emission 488 nm/615 nm). Cyto-dye is permeable to the cell membrane, therefore live and dead cells appeared green. Propidium iodide is impermeable to live cell membranes so only dead cells were marked red. The Nikon Ti-E microscope equipped with FITC and Texas red filters was used to image the cells. Cell counting was performed using ImageJ.

Example 9. Cells Grown on as-Prepared Multilayers

Variables in polyelectrolyte multilayers (PEMUs) include the polyelectrolytes with which they are made, the thickness of the film, the salt concentration, which polymer is on "top" (i.e. added last) and, for weak polyelectrolytes, the pH at which the multilayer is built. The functional groups on the PDADMA/PSS system are not pH-sensitive over usual experimental ranges. Thus, variables were the thickness of the multilayer and the surface charge, which is generally believed to depend on which "layer" was added last (i.e. positive for PDADMA and negative for PSS). The thickness of PEMUs depends on the salt concentrations from which they are grown: the thickness of PDADMA/PSS is roughly proportional to the [NaCl] up to 1.5M NaCl. Thickness is correlated to the mechanical properties of the film, which are influenced by the proximity of the substrate. For example, the effective modulus sensed by cells on multilayers increases for thinner multilayers.

TABLE 1

Characteristics of the four multilayer films.

| Film | Characteristics |
| --- | --- |
| [PDADMA/PSS, 1.0]$_{10}$ | Thick film, with more negatively charged surface |
| [PDADMA/PSS, 0.15]$_{10}$ | Thin film, with minimally negatively charged surface |
| [PDADMA/PSS, 1.0]$_{10}$[PDADMA, 1.0] | Thick film, with more positively charged surface |
| [PDADMA/PSS, 0.15]$_{10}$[PDADMA, 0.15] | Thin film, with minimally positively charged surface |

3T3 fibroblast behavior on multilayers was recorded, using live cell imaging (which avoids artifacts from fixing), after three days of culture on the surfaces. See FIGS. 1A through 1E, which are bright field images acquired on day 3 of live 3T3 fibroblasts seeded at 10000 cells/cm$^2$ onto PDADMA/PSS polyelectrolyte multilayers prepared at different salt concentration. To probe response to surface charge and thickness, cells were initially cultured on four multilayers:

(FIG. 1A) [PDADMA/PSS, 1.0]$_{10}$ (PSS ending layer),
(FIG. 1B) [PDADMA/PSS, 0.15]$_{10}$ (PSS ending layer),
(FIG. 1C) [PDADMA/PSS, 1.0]$_{10}$[PDADMA, 1.0] (PDADMA ending layer), and
(FIG. 1D) [PDADMA/PSS, 0.15]$_{10}$[PDADMA, 0.15] (PDADMA ending layer).

Figure 1E:
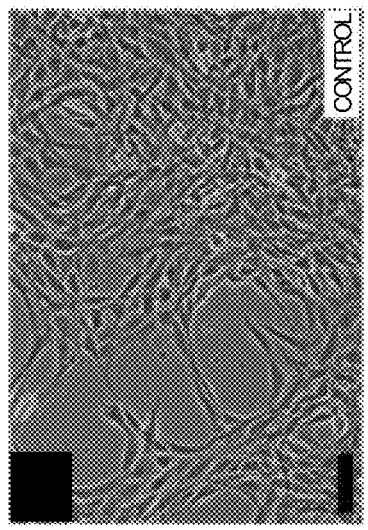
Figure 1B:
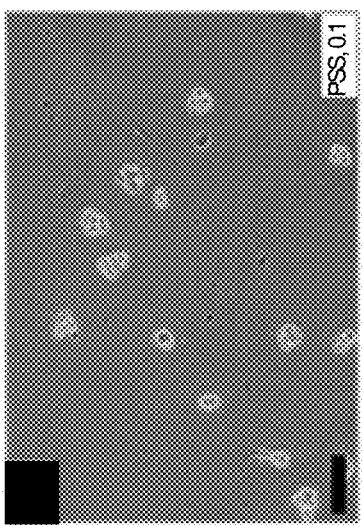
Figure 1D:
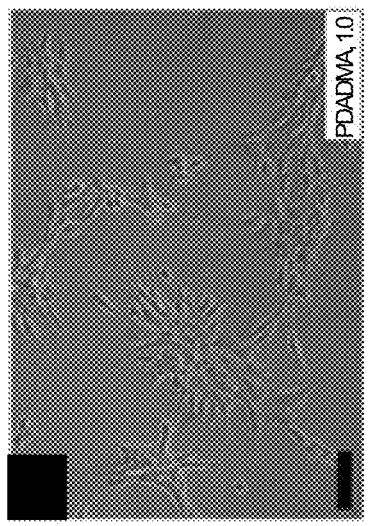
Figure 1A:
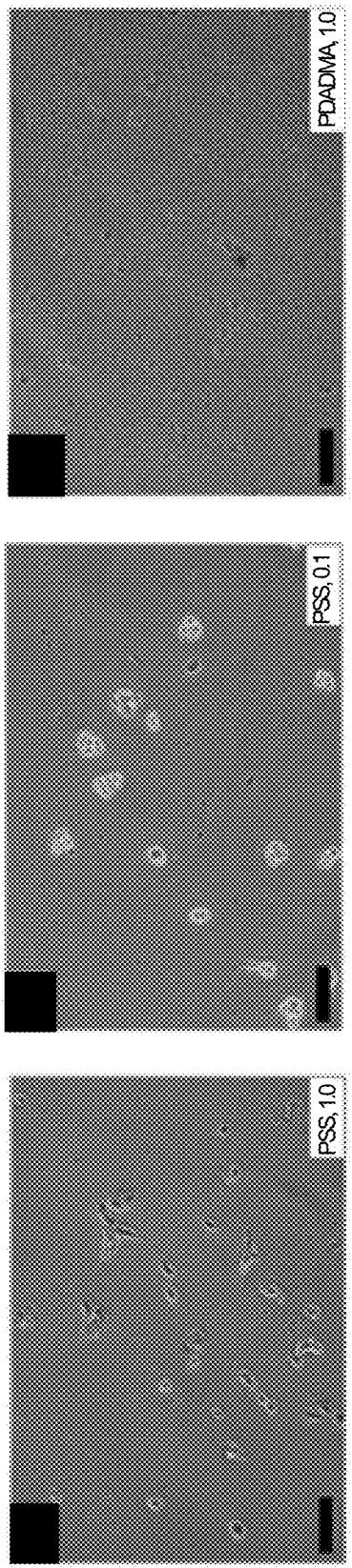

Of these surfaces, only [PDADMA/PSS, 0.15]$_{10}$ [PDADMA, 0.15], FIG. 1D, yielded morphology and coverage approaching the control, FIG. 1E (a polystyrene "tissue culture" plate optimized, using proprietary methods, by the manufacturer for cell adhesion and proliferation).

Cells on the two PSS-ending surfaces (FIGS. 1A and 1B) displayed no signs of toxicity, rounded morphology, were poorly-spread and showed low proliferation in comparison to the control. From mechanical properties arguments, these should be well adhered, as PSS terminated surfaces are stiff, with modulii in the range of 10 MPa. In addition, the thickness of the thinner PEMU allows the stiff (plastic) substrate to enhance considerably the effective modulus the cells "feel." Using the estimates of Mehrotra et al. (see Mehrotra, S.; Hunley, S. C.; Pawelec, K. M.; Zhang, L. X.; Lee, I.; Baek, S.; Chan, C., Cell Adhesive Behavior on Thin Polyelectrolyte Multilayers: Cells Attempt to Achieve Homeostasis of Its Adhesion Energy. Langmuir 2010, 26, (15), 12794-12802), who studied the relation between thickness, stiffness and cells on PDADMA/PSS multilayers and provided a model for effective modulus based on finite difference analysis, the thin PEMU (FIG. 1B) is well within the range for strong substrate influence. If anything, the cells on the thicker PEMU (FIG. 1A) spread a little better.

Mendelsohn et al. (see Mendelsohn, J. D.; Yang, S. Y.; Hiller, J.; Hochbaum, A. I.; Rubner, M. F., Rational design of cytophilic and cytophobic polyelectrolyte multilayer thin films. Biomacromolecules 2003, 4, (1), 96-106), showed how the properties of a PEMU from poly(allylamine) and poly(acrylic acid) could be tuned from cell adhesive to cell rejecting by selection of multilayer deposition conditions. The pH dependence of these two polyelectrolytes was exploited to vary the charge balance between them. In contrast to our results, they observed cell adhesion on (presumably stiffer), less swollen, more ionically cross-linked PEMUs. This behavior was rationalized using arguments based on the hydration of the entire film, rather than surface properties, as they found response did not depend on the terminating polyelectrolyte.

Figure 2:
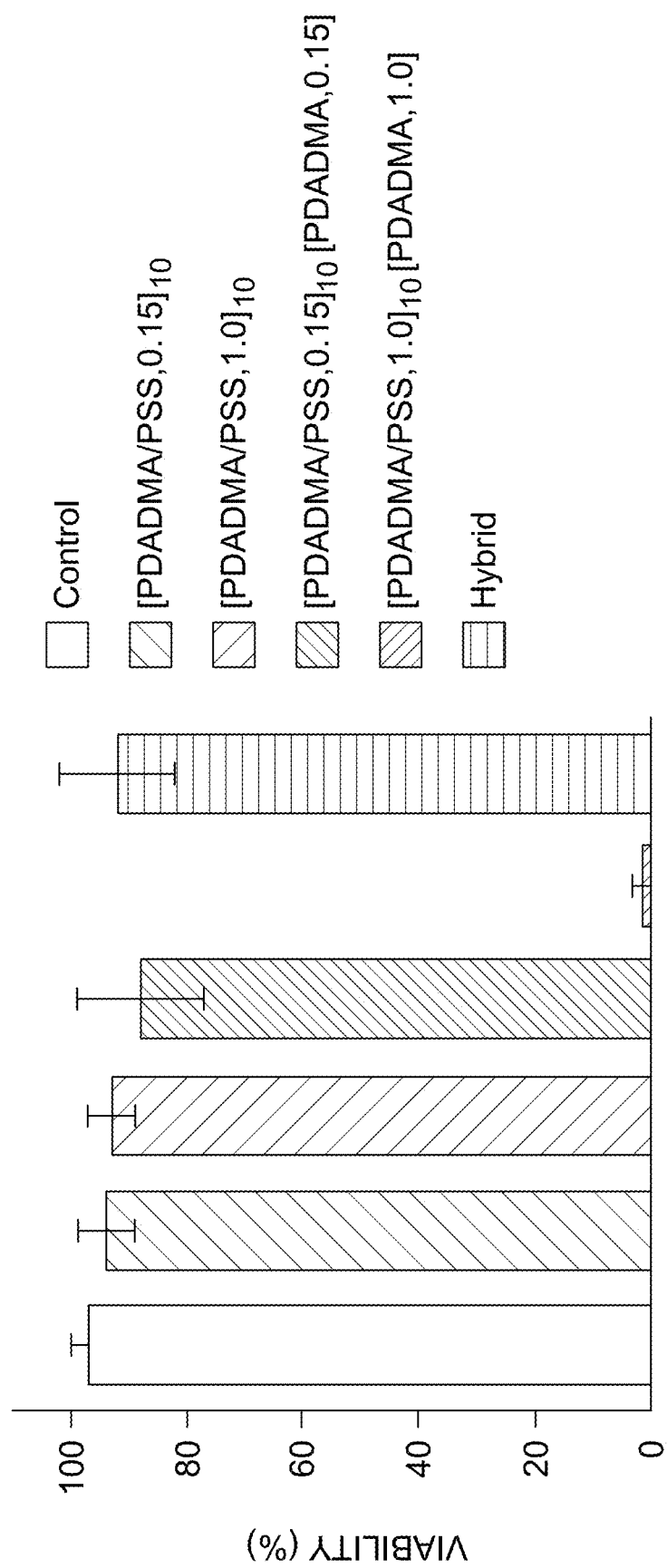
FIG. 2 is a chart depicting viability obtained at day 3 for 3T3 fibroblasts cells on [PDADMA/PSS] multilayers using Live/Dead double staining. Cells were originally seeded at a concentration of 1.5×105 cells/well. Viability on the hybrid system was determined 48 h after reseeding cell clusters on polystyrene.

PSS-terminated polyelectrolyte multilayers (PEMUs) showed no evidence of toxicity. Viability of cells on these surfaces using live/dead double staining show results comparable to the control. See FIG. 2, which is a chart depicting viability obtained at day 3 for 3T3 fibroblasts cells on [PDADMA/PSS] multilayers using Live/Dead double staining. Cells were originally seeded at a concentration of 1.5×105 cells/well. Viability on the hybrid system was determined 48 h after reseeding cell clusters on polystyrene. However, cell detachment from the PSS-terminated multilayers was observed. Many of the detached cells floated as aggregates in the media. To address the question of whether these floating cells were dead as a result of PEMU toxicity, the supernate containing these aggregates was transferred to fresh 6-well tissue culture plates. Floating cells adhered to this control surface and spread, demonstrating that the poor adhesion and detachment of cells to PSS-terminated PEMUs was not a result of cytotoxicity. The non-toxicity of PSS-terminated PEMUs is in accord with previous reports of negative-terminated PEMUs.

Fibroblasts on PDADMA-ending surfaces behaved differently depending on the salt concentration used to prepare the multilayer. Cells on [PDADMA/PSS, 0.15]$_{10}$ [PDADMA, 0.15] exhibited similar morphology to control cells, with good spreading and good cell viability. See FIG. 2. However, cells on [PDADMA/PSS, 1.0]$_{10}$[PDADMA, 1.0] were dead and the multilayer was covered with small blobs of residue. Additional experiments proved that these blobs came from the media, most likely due to proteins present in serum, as previously observed by Richert et al. (see Richert, L.; Boulmedais, F.; Lavalle, P.; Mutterer, J.; Ferreux, E.; Decher, G.; Schaaf, P.; Voegel, J.-C.; Picart, C., Improvement of stability and cell adhesion properties of polyelectrolyte multilayer films by chemical cross-linking. Biomacromolecules 2004, 5, (2), 284-294.)

Comparison of the two PDADMA-terminated PEMUs offers partial consistency with the idea that cells adhere and spread better to stiff surfaces. For the "thin" [PDADMA/PSS, 0.15]$_{10}$[PDADMA, 0.15], where coupling with the substrate would make the apparent stiffness high, cells adhered and spread well (FIG. 1D). Viability was good (FIG. 2) suggesting no toxicity. Thicker PDADMA-terminated PEMUs (which should appear softer to cells), instead of simply reducing adhesion, proved to be cytotoxic. See FIG. 1C and FIG. 2.

The stark difference in toxicity for the two positively-charged surfaces may be understood by comparing their charge densities. For example, PEMUs with free cationic chain segments were shown (by Lichter, J. A.; Van Vliet, K. J.; Rubner, M. F., Design of Antibacterial Surfaces and Interfaces: Polyelectrolyte Multilayers as a Multifunctional Platform. Macromolecules 2009, 42, (22), 8573-8586) to be more toxic towards bacteria if they were prepared under conditions which lead to more surface positive extrinsic charge. PDADMA deposited from solutions of higher salt concentrations gives a thicker layer (higher positive surface charge density). While tetraalkylammonium groups such as the one in PDADMA are known to be highly toxic towards cells (both eukariotic and prokariotic), this toxicity is moderated if the extrinsic charge density can be lowered. Thus, PAH toxicity is eliminated by pairing the cationic repeat units with anionic repeat units in PEMUs.

Though "thick" PDADMA-terminated multilayers are much softer than those of the same thickness terminated with PSS, 36 cytotoxicity of the former surface prevents comparisons of adhesion based on mechanical and surface charge.

Example 10. Cell Growth on Multilayers Made from Hydrid-Salt Conditions

In order to provide "thick" and "thin" films with more comparable charge density, a set of multilayers assembled under "hybrid" conditions of salt concentration was prepared. The object was to keep the bulk of the PEMU assembly consistent and vary only the surface charge sign and density.

Four types of hybrid multilayers were constructed:
[PDADMA/PSS, 1.0]$_9$[PDADMA, 1.0][PSS, 0.15],
[PDADMA/PSS, 1.0]$_{10}$[PDADMA, 0.15],
[PDADMA/PSS, 0.15]$_9$[PDADMA, 0.15][PSS, 1.0], and
[PDADMA/PSS, 0.15]$_{10}$[PDADMA, 1.0].

In other words, "thick" films were prepared from 1.0 M NaCl but last layer was deposited from low [NaCl] which should yield low surface charge density.

Table 2 summarizes the properties of these hybrid salt (or "hydrid") multilayers (h-PEMUs). Along with the previous PEMUs summarized in Table 1, these cover all combinations of thickness, charge, and charge density. Importantly, the hybrid salt PEMUs do not include the toxic thick/high positive charge density system described above.

TABLE 2

Characteristics of the four hybrid multilayer films.

| Hybrid Film | Characteristics |
| --- | --- |
| [PDADMA/PSS, 1.0]$_9$[PDADMA, 1.0] [PSS, 0.15] | Thick film, with minimally negatively charged surface |
| [PDADMA/PSS, 1.0]$_{10}$[PDADMA, 0.15] | Thick film, with minimally positively charged surface |
| [PDADMA/PSS, 0.15]$_9$[PDADMA, 0.15] [PSS, 1.0] | Thin film, with more negatively charged surface |
| [PDADMA/PSS, 0.15]$_{10}$[PDADMA, 1.0] | Thin film, with more positively charged surface |

FIGS. 3A through 3D show the response of cells on the h-PEMUs. FIGS. 3A through 3D are bright field live cell images acquired on day 3 of 3T3 fibroblasts seeded at 10000 cells/cm$^2$ onto hybrid-salt PDADMA/PSS polyelectrolyte multilayers prepared at different salt concentration.

(FIG. 3A) [PDADMA/PSS, 1.0]$_9$[PDADMA, 1.0][PSS, 0.15] (PSS ending layer), (FIG. 3B) [PDADMA/PSS, 0.15]$_9$[PDADMA, 0.15] [PSS, 1.0] (PSS ending layer), (FIG. 3C) [PDADMA/PSS, 1.0]$_{10}$[PDADMA, 0.15] (PDADMA ending layer), and (FIG. 3D) [PDADMA/PSS, 0.15]$_{10}$[PDADMA, 1.0] (PDADMA ending layer).

In each figure, the Scale bar is 100 µm. All surfaces showed sub-optimal adhesion and spreading compared to control. See FIG. 1E. On three of the four surfaces cells were attached as individuals and aggregates. None of the surfaces showed cytotoxicity, even the thin film with "high" positive polyelectrolyte density. This density proved toxic for the thicker films. See FIG. 1C. We hypothesize that the reason for the lack of toxicity of the thinner 1.0 M PDADMA terminated films is that only a fraction of PDADMA is added to this multilayer compared to a complete 1.0M salt film, therefore the charge density on the surface is lower. The absence of small blobs of residue on the surface, which is a characteristic of "thick" PDADMA terminated films, supports this hypothesis.

Figure 3A:
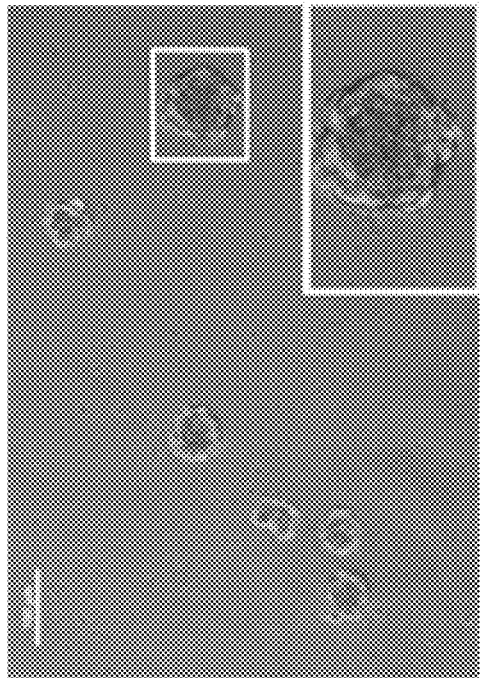
FIGS. 3A through 3D are bright field live cell images acquired on day 3 of 3T3 fibroblasts seeded at 10000 cells/cm² onto hybrid-salt PDADMA/PSS polyelectrolyte multilayers prepared at different salt concentration.
Figure 3B:
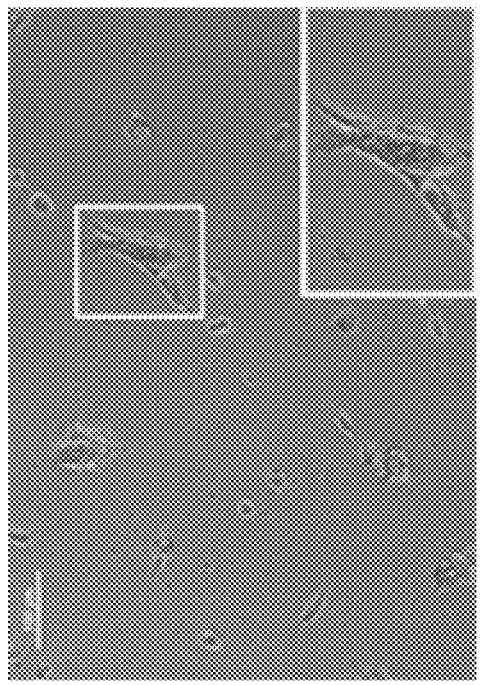
Figure 3C:
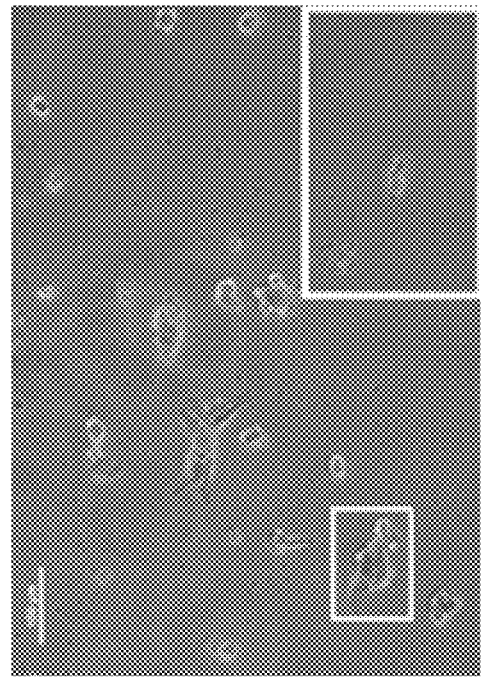
Figure 3D:
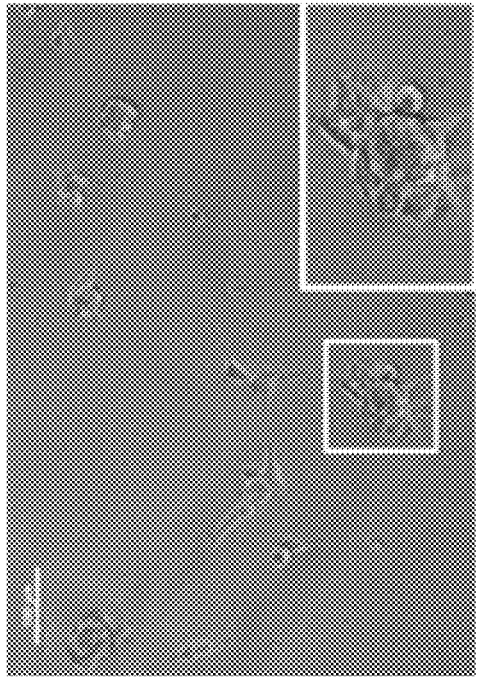

The most interesting feature in the PSS-terminated h-PEMUs is revealed by a comparison of [PDADMA/PSS, 1.0]$_9$[PDADMA, 1.0][PSS, 0.15] and [PDADMA/PSS, 0.15]$_9$[PDADMA, 0.15][PSS, 1.0]. Whereas the morphology of cells on the "thick" PSS-terminated multilayers with "low" surface charge (FIG. 3A) compares with those on the "thick" PSS with "high" charge (FIG. 1A) and those on "thin" PSS with "low" charge (FIG. 1B), the "thin" PSS-terminated h-PEMU with "high" surface charge induces an unusual cluster morphology (FIG. 3B). In this morphology, all cells are aggregated into quasispherical clusters, where approximately 75% of the total cell population formed clusters containing fewer than 40 cells, and the rest of the cells formed into macro-clusters (50 cells and up). No individual cells were seen attached and no flattening or spreading was observed.

Aggregates of cells on PEMUs are commonly observed (see for example, the aggregates in FIGS. 1A, 1B, 3A, 3C above), but well-defined quasispherical clusters have not been seen. The spherical nature of the clusters was clearly evident when the culture dish was moved slightly and the clusters were observed to roll. Clusters formation was observed as follows: at first the cells scanned the surface, extending lamellipodia and filopodia, seeking an optimal place to adhere and spread. After a while cells started to bind to each other and they interrogated the surface as a small cluster. This cell-cell assembly continued adding more cells in its path until the larger cluster formed between 48 and 72 hours after seeding. The multi-cell spheroid stopped scanning the surface and rolled freely on top of the PEMU. Fibroblast aggregation has been previously reported. Fibroblast aggregation can be caused by mechanisms such as controlling culture conditions (centrifugation, hanging drops, and rotary cell culture systems using non-adhesive or mechanically unstable surfaces, and by modifying growth factor environments during culture.)

In the present invention, no mechanical agitation was required and no mechanism to force the cells together, e.g., by gravity, was employed. Cells spontaneously aggregated by encounters on the flat substrate.

Figure 4B:
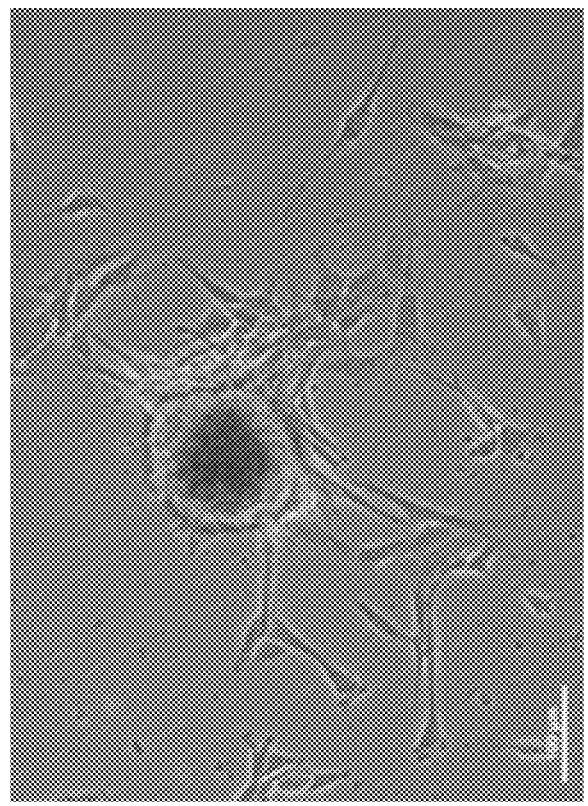
FIGS. 4A and 4B are bright field images of live fibroblasts.
Figure 4A:
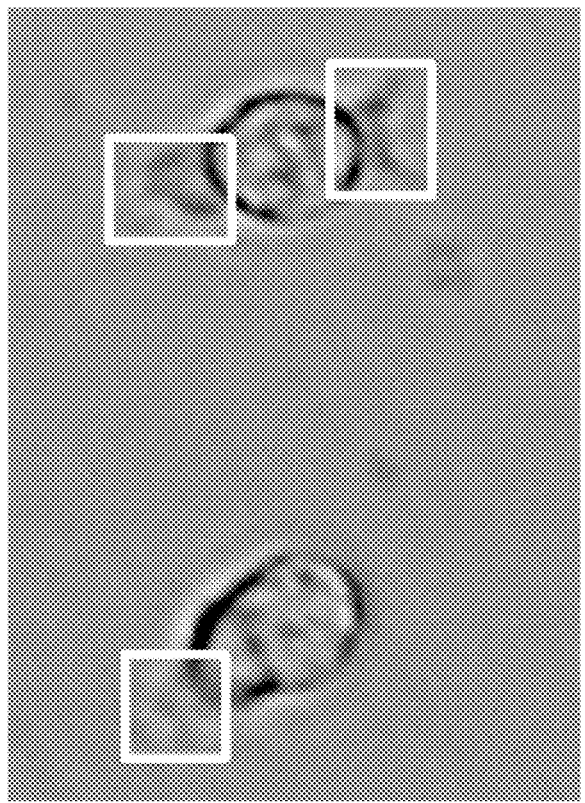

FIGS. 4A and 4B are bright field images of live fibroblasts. (FIG. 4A) Frame from live cell imaging of individual cells scanning the surface of a [PDADMA/PSS, 0.15]$_9$ [PDADMA, 0.15][PSS, 1.0] film, the cells extend their lamellipodia (highlighted in boxes) in different directions but do not attach to the substrate. Scale bar 10 µm. (FIG. 4B) fibroblasts leaving a quasi-spherical cluster after being reseeded onto an uncoated polystyrene control surface. Scale bar 100 µm. The video also addresses the question of whether cells in clusters are viable. After 72 hours the clusters were removed from the supernate and plated onto the polystyrene tissue culture control surface, whereupon cells started to separate from the cluster and attach to the polystyrene. A frame from the video is depicted in FIG. 4A, showing the fibroblasts plating out from clusters onto polystyrene.

After 48 hours, long enough to allow most of the cells to separate from clusters and spread on the surface, the viability of these plated cells was measured. The viability was 92%, revealing that while the film prevents cell adhesion, it is non-toxic, at least during the three days of exposure. See FIG. 2. This trend was also observed with the two hybrid films with PDADMA ending layer (FIG. 1C and FIG. 1D), in which both were non-toxic. When compared to [PDADMA/PSS, 1.0]$_{10}$[PDADMA, 1.0] where all the cells were killed and a significant amount of serum components were attracted to surfaces, the hybrid version [PDADMA/PSS, 1.0]$_{10}$[PDADMA, 0.15] was not only non-toxic, but also allowed cell adhesion and the multilayer surface looked clean.

In order to confirm that the main difference between these hybrids and the native films lies on the surface of the multilayer and not within the bulk structure, a series of experiments to characterize the physical and chemical properties of these films was performed. These experiments focused on PSS-ending surfaces, specifically [PDADMA/PSS, 0.15]$_9$[PDADMA, 0.15][PSS, 1.0] (HYBRID) due to its cell resistance surface. This film will be compared with the two PSS ending layer native films [PDADMA/PSS, 0.15]$_{10}$ (NATIVE 0.15M) and [PDADMA/PSS, 1.0]$_{10}$ (NATIVE 1.0M).

Example 11. Atomic Force Microscopy: Thickness and Roughness

To further elucidate the factor(s) directing cells to cluster or not, certain variables must be excluded. For example, surface roughness is often cited as an important surface morphology feature in cell adhesion and growth. Surface roughness is ideally measured under the conditions of cells growth. Hence, AFM was used to image the various PSS-terminated surfaces under wet and dry conditions in an effort to identify features that might promote cluster formation. FIGS. 5A through 5F are 20×20 μm AFM images acquired in dry and wet conditions of hybrid and native PDADMA/PSS polyelectrolyte multilayers PSS ending layer. (FIG. 5A) dry Native 0.15M, (FIG. 5B) wet Native 0.15M, (FIG. 5C) dry Native 1.0M, (FIG. 5D) wet Native 1.0M, (FIG. 5E) dry Hybrid, (FIG. 5F) wet Hybrid. See also Table 3, providing the dry and wet thickness and roughness of three different PSS ending multilayers.

FIGS. 5A through 5D show AFM images of PSS-terminated surfaces made from 0.15 and 1.0M NaCl (FIGS. 5A, 5B, 5C, 5D) and the cluster-inducing [PDADMA/PSS, 0.15]$_9$[PDADMA, 0.15][PSS, 1.0]

TABLE 3

Comparison of dry and wet thickness and roughness of three different PSS ending multilayers.

|  | Native 0.15M | Native 1.0M | Hybrid |
|---|---|---|---|
| Dry thickness (nm) | 38 ± 3 | 411 ± 11 | 45 ± 3 |
| Dry roughness (nm) | .6 ± 0.6 | 45 ± 3 | 1.5 ± 0.4 |
| Wet thickness (nm) | 58 ± 4 | 498 ± 30 | 63 ± 5 |
| Wet roughness (nm) | 1.9 ± 0.6 | 54 ± 5 | 1.8 ± 0.3 |

In the case of 3T3 fibroblasts, Prasad et al. (see Prasad, B. R.; Brook, M. A.; Smith, T.; Zhao, S.; Chen, Y.; Sheardown, H.; D'Souza, R.; Rochev, Y., Controlling cellular activity by manipulating silicone surface roughness. Colloids and Surfaces B: Biointerfaces 2010, 78, (2), 237-242) illustrated that these cells attach and proliferate better on smooth surfaces ~88 nm). Our results comparing the hybrid and native films show both are very smooth and there are no significant differences in thickness and roughness. See Table 3. This is an anticipated result due to the similar deposition conditions of the two multilayers, which only differ from each other in the last layer. These two films also differ considerably in thickness and roughness compared to the Native 1.0M multilayer, again this result was expected due to the fact the higher the salt concentration the more polymer is deposited on each layer and thicker films are rougher. Both of the native films allowed cell adhesion even with the evident differences in thickness and roughness, however the hybrid film prevents cell adhesion even with similar characteristics to one of the native multilayers. Therefore, it is possible to assume that for cells on PSS ending multilayers, thickness and roughness are not determining factors for cell adhesion.

Example 12. Contact Angle and X-Ray Photoelectron Spectroscopy

Surface hydrophilicity is often cited as an important variable for protein adsorption and cell adhesion. For example, Janssen et al. (see Janssen, M. I.; van Leeuwen, M. B. M.; Scholtmeijer, K.; van Kooten, T. G.; Dijkhuizen, L.; Wosten, H. A. B., Coating with genetic engineered hydrophobin promotes growth of fibroblasts on a hydrophobic solid. Biomaterials 2002, 23, (24), 4847-4854) reported that fibroblasts prefer moderately hydrophilic surfaces. The air-water-surface contact angle is usually employed as a gauge of relative hydrophilicity. Table 4 summarizes static water contact angles on three comparison PSS PEMUs. Contact angles were similar for all surfaces, those on the native 1.0M and hybrid being indistinguishable—a reasonable result given the last PSS layer was deposited under the same conditions. Therefore, hydrophilicity, as interpreted from wettability, does not appear to be a significant cause of the difference in cell behavior between native and hybrid films.

TABLE 4

Static contact angle measurements of three different PSS ending multilayers.

| Type of film | Water contact angle | XPS S:N ratio |
|---|---|---|
| Native 0.15M | 31 ± 1 | 0.94 |
| Native 1.0M | 27 ± 2 | 0.98 |
| Hybrid | 27 ± 4 | 1.6 |

Additional information on the composition of the surface was sought with X-ray photoelectron spectroscopy, XPS, using 2 pS and 1 sN electrons to probe the respective concentrations of sulfonate and tetraethylammonium for the first 8 nm of the film surface. Raw XPS spectra are shown in Supporting Information. The surfaces for the two native PEMUs had stoichiometric (1:1) ratios of S:N. This counterintuitive result was recently explained by the absence of overcompensation by PSS (see Ghostine, R. A.; Markarian, M. Z.; Schlenoff, J. B., Asymmetric Growth in Polyelectrolyte Multilayers. J Am Chem Soc 2013, 135, (20), 7636-7646). In this multilayer growth model, overcompensation is observed only with PDADMA. In contrast, the hybrid film had a 1.6 S:N ratio, demonstrating some degree of overcompensation by PSS. This overcompensation implies a higher negative ($—SO^{3-}$) surface charge density for the hybrid film.

Example 14. Total and Surface Charge

Figure 6:
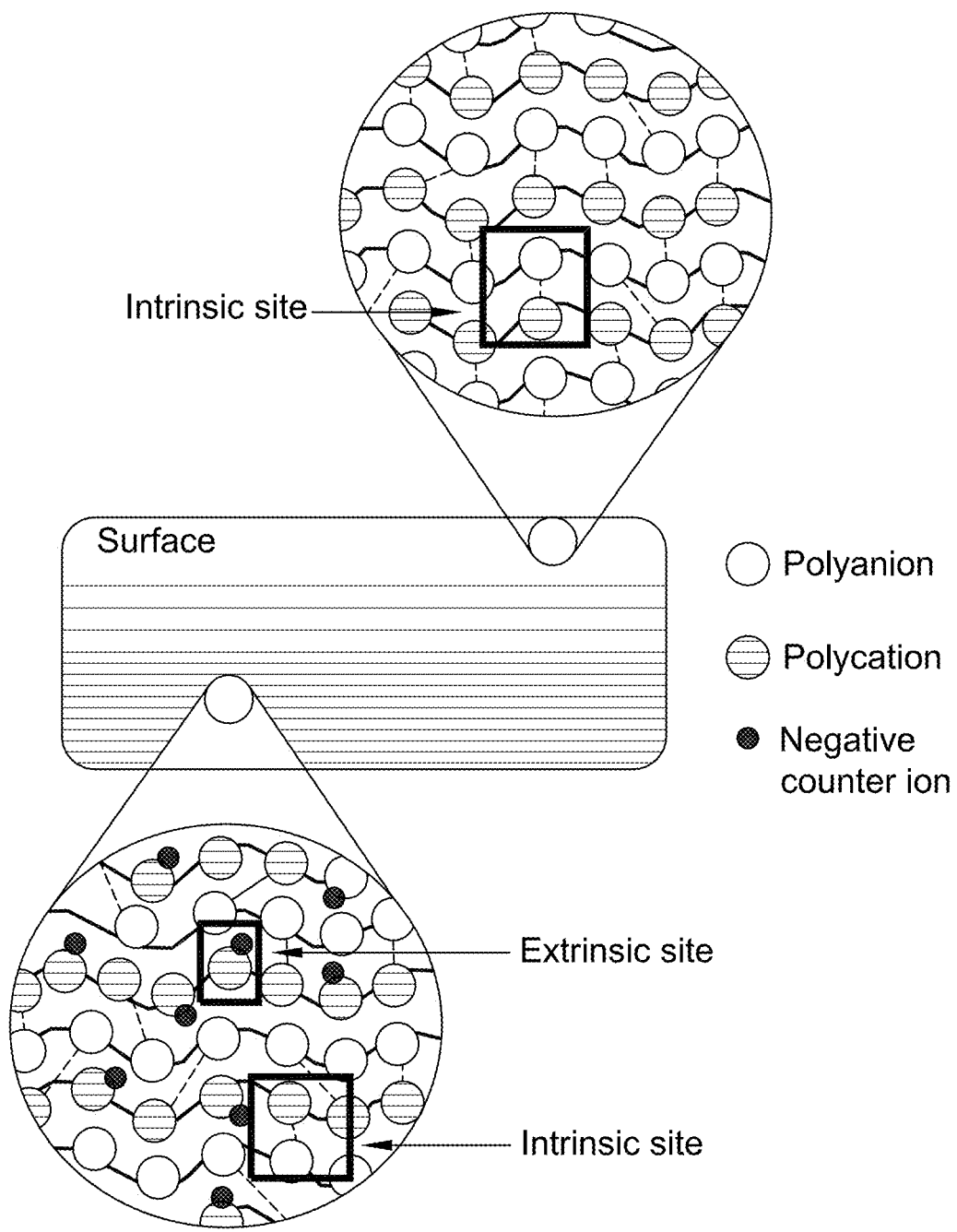
FIG. 6 is an illustration depicting the differences between surface and bulk ionic network for a PDADMA/PSS multilayer. Extrinsic sites in the multilayer can be exchanged with radiolabeled counterions.

Relatively thick (greater than about 12 layers) PDADMA/PSS multilayers built at room temperature have a "skin" morphology, with a glassy, stoichiometric (i.e., intrinsic) layer of PDADMA/PSS on top of a blanket of "extrinsic" complex with excess PDADMA. Because the skin is intrinsic it has a much greater modulus than the rest of the PEMU. This morphology is illustrated in FIG. 6, which is an illustration depicting the differences between surface and bulk ionic network for a PDADMA/PSS multilayer. Extrinsic sites in the multilayer can be exchanged with radiolabeled counterions.

As shown in Scheme 1, extrinsic charge is defined as polyelectrolyte repeat units compensated by counterions. Labeling techniques have been developed for exchanging these counterions with radiolabeled counterions, which provides, unambiguously and accurately, the ion content of PEMUs (i.e., the extrinsic charge). The selection of radiolabel depends on whether positive or negative extrinsic charge is sought. Cations label negative extrinsic charge and anions label positive extrinsic charge. $^{22}Na^+$ is an ideal isotope for use in the present case because it self-exchanges with the nonradioactive $^{23}$Na$^+$ populating the multilayer. $^{125}$I$^-$ has properties similar to Cl$^-$. Both of these isotopes gave acceptable counting efficiencies of >25% using a scintillator/PMT apparatus. Calibration curves were acquired for each isotope. Sufficient counts were obtained to reduce total negative and positive intrinsic charge, respectively, within the PEMU.

Scheme 1. Extrinsic charges, paired with counterions, are more available for interactions than intrinsic changes.

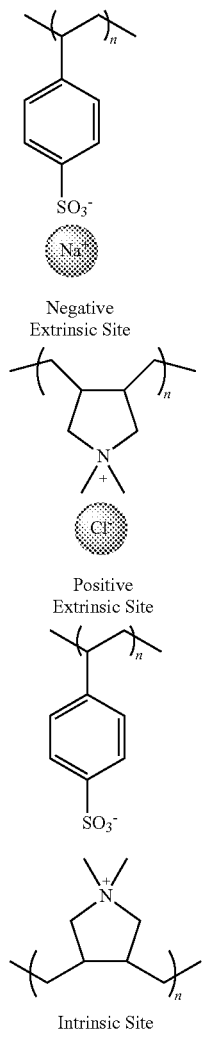

Figure 7A:
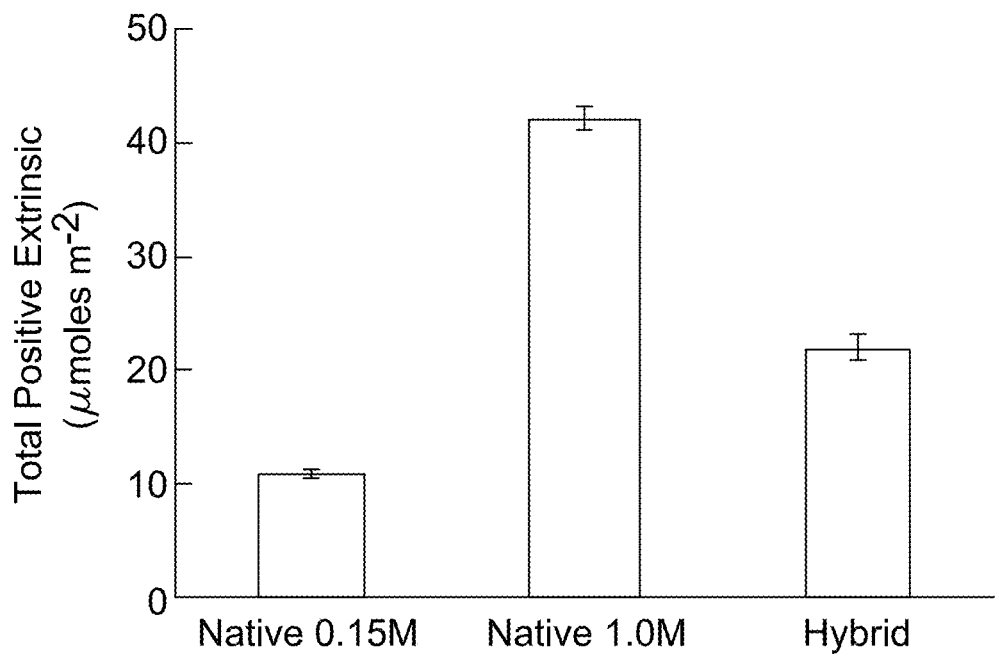
FIG. 7A is a graph depicting total positively charged extrinsic sites in PDADMA/PSS multilayers ending with PSS. $^{125}$I was exchanged with Cl$^-$ and counted using a plastic scintillator and a photomultiplier tube.
Figure 7B:
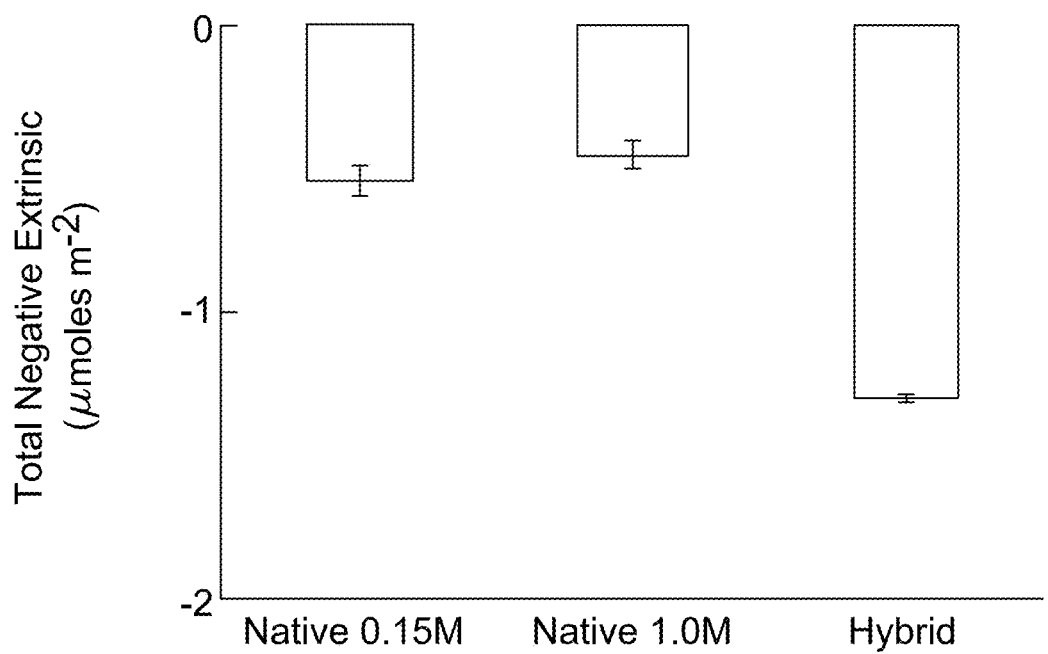
FIG. 7B is a graph depicting total negatively charged extrinsic sites of the same PSS/PDADMA multilayers. $^{22}$Na was exchanged with $^{23}$Na.

Given the strong dependence of PEMU modulus on extrinsic site density, the total positive extrinsic density was measured with $^{125}$I, as seen in FIGS. 7A and 7B, presented as both the areal density (moles m$^{-2}$). FIG. 7A is a graph depicting total positively charged extrinsic sites in PDADMA/PSS multilayers ending with PSS. $^{125}$I was exchanged with Cl$^-$ and counted using a plastic scintillator and a photomultiplier tube. FIG. 7B is a graph depicting total negatively charged extrinsic sites of the same PSS/PDADMA multilayers. $^{22}$Na was exchanged with $^{23}$Na.

Native 0.15M films have the lowest amount of total positive extrinsic sites, native 1.0M films have the highest amount of positive extrinsic sites, while h-PEMUs fall somewhere in between. Residual positive polymer charge was expected in the films due to overcompensation by PDADMA during the preparation of the multilayer. This residual positive charge is a small fraction of the total charge of all the polyelectrolyte in the film (approximately 1.4 mmoles m$^{-2}$ for a 400 nm thickness film and 0.14 mmoles m$^{-2}$ for a 40 nm thickness film).

Total negative extrinsic sites were measured by exchanging $^{23}$Na$^+$ ions inside the multilayer with radioactive $^{22}$Na$^+$. See FIG. 7B. As determined previously, there are negligible amounts of sodium within native multilayers, meaning there is negligible extrinsic negative charge (all —SO$^{3-}$ groups are compensated by +DADMA repeat units).

The sign of the charge on the surface of a PEMU is commonly determined via surface electrokinetic measurements, such as streaming potential, electrophoretic flow, or electroosmotic flow. Unfortunately, such electrokinetic techniques drastically underestimate the surface concentration of counterions, since most of these ions are adsorbed to the surface in the Stern layer and are not advected by the solution streaming next to the surface. Displacement or exchange of these counterions is a strong driving force in protein adsorption to multilayers.

Figure 8:
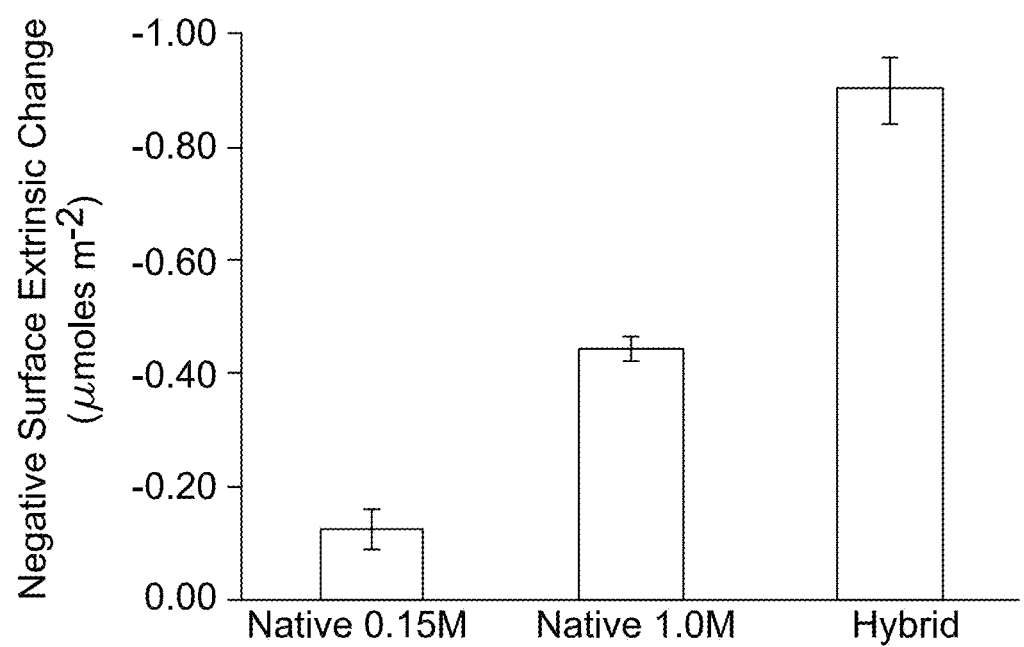
FIG. 8 is a graph depicting negative fixed surface charge density data of PDADMA/PSS multilayers ending with PSS. $^{14}$C-tetraethylammonium bromide was exchanged with surface cations.

It has been discovered that the $^{14}$C-tetraethylammonium ion is excluded from the bulk of multilayers capped with PSS (see Ghostine, R. A.; Markarian, M. Z.; Schlenoff, J. B., Asymmetric Growth in Polyelectrolyte Multilayers. J Am Chem Soc 2013, 135, (20), 7636-7646). Tetraethylammonium is apparently too large to diffuse through the PEMU but it is well suited to exchanging with cations at the surface. The procedure for determining surface extrinsic negative charge was simply to immerse the substrate in 10$^{-4}$ M $^{14}$C-tetraethylammonium and then blow the excess liquid off with a jet of nitrogen gas. The detection limit for this method was about 0.07 μmoles m$^{-2}$ or about 3% of a monolayer. FIG. 8 shows comparisons between the surface charges of three PSS-terminated PEMUs. The surface charge for native 0.15M was 0.13 μmoles m$^{-2}$ while the native 1.0 M had a charge density of 0.44 μmoles m$^{-2}$. Interestingly, the hybrid surface showed the highest charge density of 0.90 μmoles m$^{-2}$. See FIG. 8.

These differences in surface charge density of ions are major distinctions between the three PSS multilayers. The hybrid surface is almost nine times more negative than the native 0.15M film: but both multilayers have similar morphology and thickness (Table 3). Since they are both ultrathin, it is certain that the proximity and stiffness of the substrate yield a high effective modulus from the perspective of a cell, i.e. "substrate stiffness" is not a differentiating factor.

Example 15. Weak Interactions at the Surface of a Zwittersolid

All PSS-terminated multilayers were unfavorable for promoting cell attachment and spreading. These PEMUs were not toxic. Based on their mechanical properties, the thinner films, with a high effective modulus, should have induced cell spreading, at least for the few cells that did attach. If attachment were related to hydrophilicity, these hydrophilic PEMUs should have been as effective as glass for adhering and proliferating cells. Why do these surfaces show poor adhesive properties and what is the reason for the exceptional clustering seen on the post-deposition treated PEMU?

A possible answer starts with looking at the surface which showed the best adhesion/spreading properties: [PDADMA/PSS, 0.15]$_{10}$[PDADMA, 0.15]. See FIG. 1D. Cells do not adhere directly to surfaces. Their membrane receptors, such as integrin, which promote adhesion and instigate cell spreading, bind to specific functionality such as the RGD sequence on fibronectin. Thus, good protein adhesion to surfaces is required. Proteins are present in the growth media (serum) and are expressed and transported to the extracellular matrix by the cell. During cell culture, a mildly positive surface will cause adsorption of net negative proteins (such as fibronectin) and proteins with negative patches. (A surface with too much positive charge disrupts the cell membrane leading to cytotoxicity, FIG. 1C). With a firm layer of protein the stage is now set for the cell to adhere directly (if the appropriate ligands are present) or to displace the soft corona of major serum proteins, such as serum albumin, with the correct adhesive proteins expressed by the cell itself.

In an earlier study, we found protein adsorption properties for PDADMA/PSS multilayers depended strongly on the last layer. See Salloum, D. S.; Schlenoff, J. B., Protein Adsorption Modalities on Polyelectrolyte Multilayers. *Biomacromolecules* 2004, 5, (3), 1089-1096. PEMUs terminated with PSS adsorbed very little protein while those terminated with PDADMA acted as "sponges" absorbing large quantities of serum albumin. The adsorption of bovine serum albumin, BSA, on select PEMUs was measured here using transmission FTIR (see Supporting Information for FTIR spectra). Table 4 shows significant sorption of BSA on (into) PEMUs terminated with PDADMA, while those terminated with PSS adsorbed slightly more than, or below, the detection limit of 1.1 mg m$^{-2}$. A monolayer of BSA is about 1 mg m$^{-2}$.

The surface charge measurements in FIG. 8 are consistent with earlier findings that a PSS-terminated multilayer is almost neutral, implying complete and efficient pairing of PSS with PDADMA at the surface. See Ghostine, R. A.; Markarian, M. Z.; Schlenoff, J. B., Asymmetric Growth in Polyelectrolyte Multilayers. *J. Am. Chem. Soc.* 2013, 135, (20), 7636-7646. With little surface charge, proteins must rely on interactions other than ion pairing ("electrostatic") to adsorb, such as hydrophobic interactions (expected to be weak on a hydrophilic surface). Thus, even if a protein does adsorb it is easily stripped off the surface when tension is applied to it by the cell via the integrins which are addressing the binding sequences.

We recently characterized the intrinsic surface of a stoichiometric PEMU, such as PDADMA/PSS terminated by PSS, as having the effective composition of a zwitterion. See Schlenoff, J. B., Zwitteration: Coating Surfaces with Zwitterionic Functionality to Reduce Nonspecific Adsorption. *Langmuir* 2014, 30, (32), 9625-9636. Zwitterionic groups are widely understood to reduce or prevent protein adhesion. The best known example is the phosphatidylcholine, PC, functional group, which is prevalent at the external surface of the cell membrane. Stoichiometric polyelectrolyte complexes have equal numbers of hydrated positive and negative polymer repeat units in close proximity. We termed these stoichiometric complexes "zwittersolids." If a glassy, hydrated solid has a net surface charge approaching zero it should exhibit poor protein adsorption similar to zwitterionic functional groups. Thus, protein adheres weakly and is unable to support the mechanotransduction mechanism cells use to report a stiff surface, even though the surface is stiff.

With the mechanism proposed above, the hybrid surface is more intriguing: why does the surface need to be slightly negatively charged to cause all cells to cluster? It appears that the adhesion mechanism has switched from a surface that interacts weakly with cells to one where cell-cell interaction is preferred. Our hypothesis for greater protein repellency of the hybrid surface is that a little negative charge is required to overcome weak hydrophobic interactions (the water contact angle is not zero) with the surface. Since fibronectin and most adhesion proteins are net negative a slight negative surface repels them. A subtle balance of charge repulsion probably exists: if the negative charge density is too high the positive patches on a protein may now interact with the surface.

Some comparisons of charge density are instructive. The silanol groups on glass (silica) have a density approaching 8 μmol m$^{-2}$. See Vandervoort, P.; Gillisdhamers, I.; Vansant, E. F., Estimation of the Distribution of Surface Hydroxyl-Groups on Silica-Gel, Using Chemical Modification with Trichlorosilane. *J. Chem. Soc.—Farad. Trans.* 1990, 86, (22), 3751-3755. Their density is pH dependent, with a pK$_a$ of about 5. See Kirby, B. J.; Hasselbrink, E. F., Zeta Potential of Microfluidic Substrates: 1. Theory, Experimental Techniques, and Effects on Separations. *Electrophoresis* 2004, 25, (2), 187-202. Thus, serum albumin (net negative) adsorbs to silica with a monolayer coverage of about 1 mg m$^{-2}$ even though the adsorption is endothermic. See Kulikova, G. A.; Ryabinina, I. V.; Guseynov, S. S.; Parfenyuk, E. V., Calorimetric Study of Adsorption of Human Serum Albumin onto Silica Powders. *Thermochim. Acta* 2010, 503, 65-69. The adsorption is driven entropically by the release of counterions. If the phospholipid head group occupies about 60 Å$^2$, the density of lipids at the cell membrane is 2.8 μmol m$^{-2}$. Assuming the bulk density of complexed PDADMA and PSS is 1.2 g cm$^3$, a "monolayer" of PDADMA/PSS.10H$_2$O (i.e., 10 hydration waters per ion pair) has about 2.2 μmol m$^{-2}$ of charge-balanced polyelectrolyte pairs. The external surface of the cell membrane is mostly comprised of PC lipids but also has negative lipids. See Deleu, M.; Crowet, J.-M.; Nasir, M. N.; Lins, L., Complementary Biophysical Tools to Investigate Lipid Specificity in the Interaction Between Bioactive Molecules and the Plasma Membrane: A Review. *Biochim. Biophys. Acta* 2014, 1838, (12), 3171-3190. If 25% of the lipids are negatively charged the surface charge density would be about −0.7 μmol m$^{-2}$. This is close to the −0.9 μmol m$^{-2}$ value found for the cluster-inducing h-PEMU in FIGS. 3A through 3D. In these comparisons it is probable that the organization of the lipid head groups, i.e facing outwards, caused by the packing of the lipid tails would be more effective in reducing nonspecific adsorption than a more amorphous zwitterion-mimicking presentation of the PEMU. The role of slight negative charge in discouraging protein adsorption, therefore promoting cell clustering, is, of course, speculative at present. It is believed that the glassy nature of the thin, intrinsic h-PEMU is important in preventing any exchange or penetration of protein into the multilayer.

The following Table 4 summarizes our qualitative and quantitative findings.

TABLE 4

| Film | Thickness (nm) | surface charge | Surface charge density (μmoles m$^{-2}$) |
|---|---|---|---|
| [PDADMA/PSS, 1.0]$_{10}$ | 258 ± 12 | Negative | 0.44 |
| [PDADMA/PSS, 0.15]$_{10}$ | 38 ± 3 | Negative | 0.15 |
| [PDADMA/PSS, 1.0]$_{10}$[PDADMA, 1.0] | 279 ± 15 | Positive | — |
| [PDADMA/PSS, 0.15]$_{10}$[PDADMA, 0.15] | 42 ± 1 | Positive | — |
| [PDADMA/PSS, 1.0]$_{9}$[PDADMA, 1.0][PSS, 0.15] | 224 ± 8 | Negative | — |
| [PDADMA/PSS, 1.0]$_{10}$[PDADMA, 0.15] | 259 ± 12 | Positive | — |
| $^a$ [PDADMA/PSS, 0.15]$_{9}$[PDADMA, 0.15][PSS, 1.0] | 45 ± 3 | Negative | 0.90 |
| [PDADMA/PSS, 0.15]$_{10}$[PDADMA, 1.0] | 56 ± 3 | Negative | — |

| Film | A(b)dsorbed BSA (mg m$^{-2}$) | Roughness (nm) | Cell morphology, viability |
|---|---|---|---|
| [PDADMA/PSS, 1.0]$_{10}$ | 1.3 ± 1 | 21 ± 1.0 | Round, viable |
| [PDADMA/PSS, 0.15]$_{10}$ | <1.1 | 1.6 ± 0.6 | Round, viable |
| [PDADMA/PSS, 1.0]$_{10}$[PDADMA, 1.0] | 170 ± 10 | 5.0 ± 1.1 | Dead |
| [PDADMA/PSS, 0.15]$_{10}$[PDADMA, 0.15] | 7.9 ± 1 | 1.4 ± 0.3 | Spread similar to control, viable |
| [PDADMA/PSS, 1.0]$_{9}$[PDADMA, 1.0][PSS, 0.15] | — | 1.2 ± 0.3 | Round, viable |
| [PDADMA/PSS, 1.0]$_{10}$[PDADMA, 0.15] | — | 3.0 ± 1.0 | Round, viable |
| $^a$ [PDADMA/PSS, 0.15]$_{9}$[PDADMA, 0.15][PSS, 1.0] | <1.1 | 1.5 ± 0.4 | Spherical cluster, viable |
| [PDADMA/PSS, 0.15]$_{10}$[PDADMA, 1.0] | — | 3.2 ± 1.2 | Round, viable |

$^a$ "Hybrid"

With the introduction of excess negative polyelectrolyte charge, a thin PDADMA/PSS multilayer supports the growth of fibroblasts as a spheroid cluster of cells. Live cell imaging revealed continued interrogation of surfaces by clusters as they formed. This weak interaction may be critical, as encounters and aggregation should be more likely in 2 dimensions (on the surface) as opposed to 3 dimensions (in the media). The role of substrate stiffness in regulating cell adhesion and spreading, while clear in much prior work, appears to be less relevant for the system here, as illustrated in the contradictions mentioned above. Earlier work on stiffness cues for directing cell fate showed a dependence of motility on modulus (durotaxis). More recent publications highlight both agreement with, and divergence from, the thesis that cells migrate and adhere to stiffer areas. Recent experiments by Trappmann et al. illustrate that the fate of cells is not based on the amount of protein available on the substrate, but rather on mechanical cues related to how strongly these proteins are anchored to the surface. More study is needed on the resilience of the protein-surface interaction, which is a more difficult task than measuring the amount of adsorbed protein. A non-toxic ("biocompatible") hydrated surface which induces cells to cluster should be of use in stem cell technology, where it has been shown that stem cell pluripotency is maintained when cells form 3-D multicellular clusters. See Kurosawa, H., Methods for Inducing Embryoid Body Formation: in vitro Differentiation System of Embryonic Stem Cells. *J. Biosci. Bioeng.* 2007, 103, (5), 389-398.

Example 16. Clusters of Mesencymal Stem Cells

Figure 9C:
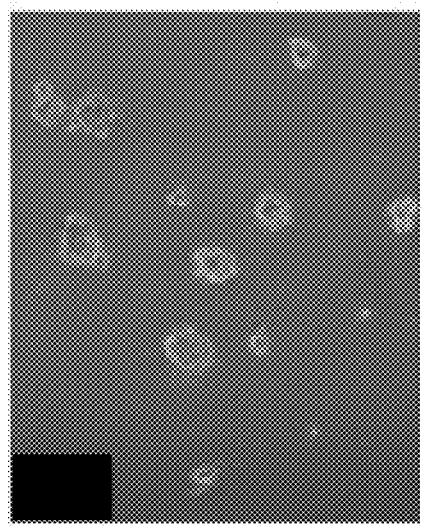
FIGS. 9A, 9B, and 9C are bright field live cell images acquired on day 3 after seeding mesenchymal stems cells onto [PDADMA/PSS, 0.15]9[PDADMA, 0.15][PSS, 1.0] multilayers.
Figure 9B:
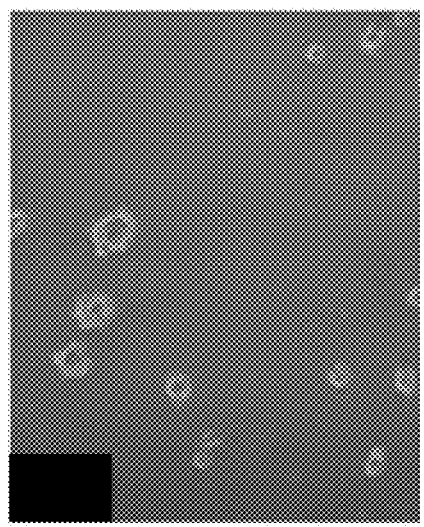
Figure 9A:
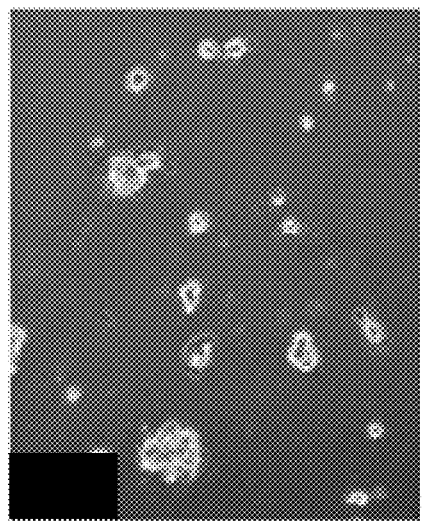

Human mesenchymal stem cells (HMSCs) were seeded at 40000 cells/well in a 12 well plate onto the following hybrid-salt polyelectrolyte multilayer [PDADMA/PSS, 0.15]9[PDADMA, 0.15][PSS, 1.0]. FIG. 9A is an image depicting HMSCs exposed to hybrid film for 24 hours. FIG. 9B is an image depicting HMSCs exposed to hybrid film for 48 hours. FIG. 9C is an image depicting HMSC exposed to hybrid film for 72 hours. The multilayers were prepared by coating tissue culture plastic 12 well plates, and the cells were cultured in DMEM, supplemented with 1 g L$^{-1}$ L-glutamine, 1.2 g L$^{-1}$ sodium bicarbonate, 10% Cosmic Calf Serum (CCS), 100 U mL$^{-1}$ penicillin G, 100 μg mL$^{-1}$ streptomycin, 0.25 μg mL$^{-1}$ amphotericin B and 10 μg mL$^{-1}$ gentamicin.

As seen in FIGS. 9A, 9B, and 9C, it is clear the formation of the clusters occurs with HMSCs, suggesting that the hybrid film behaves the same way regardless of the cell type. Additionally the clusters appeared much more quickly in this cell line.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

What is claimed:
1. An article comprising:
a layer suitable for culturing quasispherical cell clusters, the layer comprising a bulk region comprising an interpenetrating network of at least one predominantly positively charged polyelectrolyte and at least one predominantly negatively charged polyelectrolyte, a back surface region, and a front surface region, wherein the front surface region comprises a net negative fixed surface charge density of between 0.5 micromole per m$^2$ and 1.5 micromole per m$^2$, wherein the net negative fixed surface charge density is comprised of a deposited negatively charged polyelectrolyte that is obtained by mixing a negatively charged polyelectrolyte with a conditioning salt, wherein the conditioning salt is selected from the group consisting of chloride salts, citrate salts, and phosphate salts.

2. The article of claim 1 wherein the front surface region comprises a net negative fixed surface charge density of between 0.6 micromole per $m^2$ and about 1.5 micromole per $m^2$.

3. The article of claim 1 wherein the front surface region comprises a net negative fixed surface charge density of between about 0.5 micromole per $m^2$ and 1.0 micromole per $m^2$.

4. The article of claim 1 wherein the front surface region comprises a net negative fixed surface charge density of between about 0.6 micromole per $m^2$ and 1.0 micromole per $m^2$.

5. The article of claim 1 wherein the layer thickness is less than about 100 nm.

6. The article of claim 1 further comprising a substrate comprising an exposed surface, wherein the exposed surface of the substrate is in contact with the back surface region of the layer suitable for culturing quasispherical cell clusters.

7. The article of claim 6 wherein the substrate comprises a solid support comprising a material selected from the group consisting of plastic, metal, ceramic, and gel.

8. The article of claim 1 wherein the at least one predominantly negatively charged polyelectrolyte is selected from the group consisting of poly(styrenesulfonic acid) (PSS), poly(2-acrylamido-2-methyl-1-propane sulfonic acid) (PAMPS), sulfonated poly (ether ether ketone) (SPEEK), poly(ethylenesulfonic acid), and poly(methacryloxyethylsulfonic acid).

9. The article of claim 1 wherein the at least one predominantly positively charged polyelectrolyte is selected from the group consisting of poly(diallyldimethylammonium chloride) (PDADMA), poly(vinylbenzyltrimethylammonium) (PVBTA), ionenes, poly(acryloxyethyltrimethyl ammonium chloride), poly(methacryloxy(2-hydroxy)propyltrimethyl ammonium chloride), poly(N-methylvinylpyridinium) (PMVP), poly(N-methyl-2-vinylpyridinium) (PM2VP), other poly(N-alkylvinylpyridines), poly(allylaminehydrochloride) (PAH), polyvinylamine, polyethyleneimine (PEI), polysulfoniums, and polyphosphoniums.

10. A method of preparing the article of claim 1, the article comprising the layer suitable for culturing quasispherical cell clusters deposited as a coating on a substrate, the method comprising:
depositing polyelectrolyte complex on an exposed surface of the substrate, the polyelectrolyte complex comprising interpenetrating network of at least one predominantly positively charged polyelectrolyte and at least one predominantly negatively charged polyelectrolyte, the interpenetrating network comprising a back surface region in contact with the exposed surface of the substrate, a bulk region, and a front surface region; and
contacting the front surface region of the interpenetrating network with a conditioning solution comprising a predominantly negatively charged polyelectrolyte and a conditioning salt to thereby deposit the predominantly negatively charged polyelectrolyte on the front surface region of the interpenetrating network, wherein said deposition of the predominantly negatively charged polyelectrolyte fixes the negative charge density of the front surface region of the interpenetrating network to a net negative fixed surface charge density of between 0.5 micromole per $m^2$ and 1.5 micromole per $m^2$, wherein the conditioning salt is selected from the group consisting of chloride salts, citrate salts, and phosphate salts.

11. The method of claim 10 wherein the polyelectrolyte complex is deposited by alternating contact of the substrate with a first solution comprising at least one predominantly positively charged polyelectrolyte and a first salt and a second solution comprising at least one predominantly negatively charged polyelectrolyte and a second salt.

12. The method of claim 11 wherein the concentration of the conditioning salt in the conditioning solution is greater than the concentration of the first salt in the first solution and further wherein the concentration of the conditioning salt in the conditioning solution is greater than the concentration of the second salt in the second solution.

13. The method of claim 11 wherein the conditioning salt in the conditioning solution comprises an anion located at a lower position in the Hofmeister series than an anion of the first salt in the first solution and an anion of the second salt in the second solution.

14. The method of claim 10 wherein the front surface region comprises a net negative fixed surface charge density of between about 0.6 micromole per $m^2$ and about 1.5 micromole per $m^2$.

15. The method of claim 10 wherein the front surface region comprises a net negative fixed surface charge density of between about 0.5 micromole per $m^2$ and about 1.0 micromole per $m^2$.

16. The method of claim 10 wherein the front surface region comprises a net negative fixed surface charge density of between about 0.6 micromole per $m^2$ and about 1.0 micromole per $m^2$.

17. A method for culturing cells on the article of claim 1, the method comprising:
plating cells upon a front surface region of a layer suitable for culturing quasispherical cell clusters, the layer comprising a bulk region comprising an interpenetrating network of at least one predominantly positively charged polyelectrolyte and at least one predominantly negatively charged polyelectrolyte, a back surface region, and a front surface region, wherein the front surface region comprises a net negative fixed surface charge density of between 0.5 micromole per $m^2$ and 1.5 micromole per $m^2$, wherein the net negative fixed surface charge density is comprised of a deposited negatively charged polyelectrolyte that is obtained by mixing a negatively charged polyelectrolyte with a conditioning salt, wherein the conditioning salt is selected from the group consisting of chloride salts, citrate salts, and phosphate salts; wherein said plating the cells upon the front surface region of the layer induces the cells to cluster into quasispherical cell clusters.

18. The method of claim 17 wherein the front surface region comprises a net negative fixed surface charge density of between about 0.6 micromole per $m^2$ and 1.5 micromole per $m^2$.

19. The method of claim 17 wherein the front surface region comprises a net negative fixed surface charge density of between about 0.5 micromole per $m^2$ and 1.0 micromole per $m^2$.

20. The method of claim 17 wherein the front surface region comprises a net negative fixed surface charge density of between about 0.6 micromole per $m^2$ and 1.0 micromole per $m^2$.

21. The method of claim 17 wherein the quasispherical cell clusters comprise a quasispherical shape selected from the group consisting of a sphere, a tri-axial ellipsoid, an oblate ellipsoid, or a prolate ellipsoid.

22. The method of claim 17 wherein the quasispherical cell clusters comprise a quasispherical shape characterized by an aspect ratio between any two dimensions measured across the sphere of less than 2.

* * * * *